(12) United States Patent
Ito et al.

(10) Patent No.: US 10,927,185 B2
(45) Date of Patent: Feb. 23, 2021

(54) BISPECIFIC ANTIBODY FORMAT

(71) Applicant: Astellas Pharma Inc., Tokyo (JP)

(72) Inventors: Yasuhiro Ito, Tokyo (JP); Atsuo Yonezawa, Tokyo (JP)

(73) Assignee: Astellas Pharma Inc., Tokyo (JP)

(*) Notice: Subject to any disclaimer, the term of this patent is extended or adjusted under 35 U.S.C. 154(b) by 637 days.

(21) Appl. No.: 15/528,131

(22) PCT Filed: Nov. 20, 2015

(86) PCT No.: PCT/JP2015/082653
§ 371 (c)(1),
(2) Date: May 19, 2017

(87) PCT Pub. No.: WO2016/080510
PCT Pub. Date: May 26, 2016

(65) Prior Publication Data
US 2017/0306053 A1    Oct. 26, 2017

(30) Foreign Application Priority Data

Nov. 21, 2014  (JP) ................................. 2014-237172

(51) Int. Cl.
| | |
|---|---|
| C12N 5/10 | (2006.01) |
| C07K 16/46 | (2006.01) |
| C07K 16/28 | (2006.01) |
| C07K 16/00 | (2006.01) |
| C12N 15/09 | (2006.01) |

(52) U.S. Cl.
CPC ............ C07K 16/468 (2013.01); C07K 16/00 (2013.01); C07K 16/2803 (2013.01); C07K 16/2896 (2013.01); C12N 5/10 (2013.01); C07K 2317/31 (2013.01); C07K 2317/35 (2013.01); C07K 2317/55 (2013.01); C07K 2317/76 (2013.01); C07K 2317/92 (2013.01); C07K 2317/94 (2013.01); C12N 15/09 (2013.01)

(58) Field of Classification Search
CPC .......... C07K 16/00–468; C07K 16/468; C07K 2317/31; C12N 5/10
See application file for complete search history.

(56) References Cited

U.S. PATENT DOCUMENTS

| | | | |
|---|---|---|---|
| 2002/0004587 A1* | 1/2002 | Miller ..................... | C07K 16/00 530/388.8 |
| 2006/0025576 A1 | 2/2006 | Miller et al. | |
| 2006/0252096 A1* | 11/2006 | Zha ......................... | C07K 16/00 435/7.1 |
| 2008/0299120 A1 | 12/2008 | Miller et al. | |
| 2010/0233079 A1 | 9/2010 | Jakob et al. | |
| 2010/0316645 A1 | 12/2010 | Imhof-Jung et al. | |
| 2011/0110852 A1 | 5/2011 | Miller et al. | |
| 2012/0238728 A1 | 9/2012 | Miller et al. | |
| 2013/0266568 A1 | 10/2013 | Brinkmann et al. | |
| 2014/0155581 A1 | 6/2014 | Gao et al. | |
| 2014/0322221 A1 | 10/2014 | Miller et al. | |
| 2015/0133638 A1 | 5/2015 | Wranik et al. | |

FOREIGN PATENT DOCUMENTS

| | | |
|---|---|---|
| EP | 0125023 A1 | 11/1984 |
| EP | 2712872 A1 | 4/2014 |
| EP | 2857516 A1 | 4/2015 |
| JP | 2003-531588 A | 10/2003 |
| JP | 2008-538926 A | 11/2008 |
| JP | 2012-510821 A | 5/2012 |
| JP | 2012-530088 A | 11/2012 |
| JP | 2013-538204 A | 10/2013 |
| JP | 2015-508077 A | 3/2015 |
| WO | WO 01/077342 A1 | 10/2001 |
| WO | WO 2006/116657 A2 | 11/2006 |
| WO | WO 2008/024188 A2 | 2/2008 |
| WO | WO 2009/052081 A2 | 4/2009 |
| WO | WO 2010/065882 A1 | 6/2010 |

(Continued)

OTHER PUBLICATIONS

Janeway, Immuno Biology The immune system in Health and Disease, 4 edition, 1999, pp. 195-209.*
Wijesuriya et al. (Protein Expression and Purification, 2018, 149:75-83).*
Liu et al. (Biotechnology Letter, 2006, 28:1725-1730).*
Supplementary European Search Report dated Oct. 2, 2018, in EP 15861801.7.
DiGiammarino et al., "Design and Generation of DVD-Ig™ Molecules for Dual-Specific Targeting," Molecular Typing of Blood Cell Antigens In: Methods in Molecular Biology, ISSN: 1064-3745; vol. 1310, Humana PR, US, Jan. 1, 2012, 899:145-156.
Wu et al., "Generation and Characterization of a Dual Variable Domain Immunoglobulin (DVD-IG™) Molecule," Antibody Engineering, Jan. 1, 2010, 2:239-250.

(Continued)

*Primary Examiner* — Jessica H Roark
(74) *Attorney, Agent, or Firm* — Foley & Lardner LLP

(57) ABSTRACT

[Problem] Provided is a bispecific antibody with a novel format that retains high binding affinity to both antigens, and can be efficiently produced in a commercial production process.
[Means for Solution] A bispecific antibody comprising two heavy chains, two first light chains, and two second light chains, in which the heavy chains each comprise a first heavy chain variable region, a CH1 region, a first linker, a second heavy chain variable region, and a heavy chain constant region in order from the amino terminus side; the first light chains comprise a first light chain variable region and a first light chain constant region; the second light chains comprise a second light chain variable region and a second light chain constant region; the first heavy chain variable region and the first light chain variable region form a first antigen binding site; the second heavy chain variable region and the second light chain variable region form a second antigen binding site; and the first antigen binding site and the second antigen binding site recognize different antigens each other.

4 Claims, 3 Drawing Sheets
Specification includes a Sequence Listing.

(56) References Cited

FOREIGN PATENT DOCUMENTS

| WO | WO 2010/145792 A1 | 12/2010 |
|---|---|---|
| WO | WO 2012/025525 A1 | 3/2012 |
| WO | WO 2012/123949 A1 | 9/2012 |
| WO | WO 2013/006544 A1 | 1/2013 |
| WO | WO 2013/119966 A2 | 8/2013 |

OTHER PUBLICATIONS

Wu et al. "Simultaneous targeting of multiple disease mediators by a dual-variable-domain immunoglobulin," Nature Biotechnology, Nov. 1, 2007, 25(11):1290-1297.

Zuo et al., "An efficient route to the production of an IgG-like bispecific antibody," Protein Engineering, May 1, 2000, 13(5):361-367.

International Search Report dated Feb. 16, 2016, in PCT/JP2015/082653.

Miller et al., "Design, construction, and in vitro analyses of multivalent antibodies," J. Immunol., 2003, 170(9):4854-4861.

DiGiammarino et al., "Ligand association rates to the inner-variable-domain of a dual-variable-domain immunoglobulin are significantly impacted by linker design," mABs, Sep./Oct. 2011; 3(5):487-494.

Supplementary Partial European Search Report dated May 24, 2018, in EP 15861801.7.

Giuliani, Maria, "Novel Processes and Products for Recombinant Production of Biopharmaceuticals," Feb. 15, 2009, http://www.fedoa.unina.it/4104/1/Thesis_M._Giuliani,pdf, 153 pages.

Office Action dated Jul. 30, 2019, in JP 2016-560297, with English translation.

Office Action dated Feb. 21, 2020, in EP 15861801.7.

Solli et al., "Tissue- and Cell-Specific Co-localization of Intracellular Gelatinolytic Activity and Matrix Metalloproteinase 2," Journal of Histochemistry & Cytochemistry, Jun. 1, 2013, 444-461, XP055669330.

Thomas, Gary, "Furin at the cutting edge: from protein traffic to embryogenesis and disease," Molecular Cell Biology, Oct. 2002, 3:753-766.

Written Opinion dated Feb. 16, 2016, in PCT/JP2015/082653, with English translation.

\* cited by examiner

BISPECIFIC ANTIBODY FORMAT

CROSS-REFERENCE TO RELATED APPLICATIONS

This application is a National Stage application of PCT/JP2015/082653, filed Nov. 20, 2015, which claims priority from Japanese application JP 2014-237172, filed Nov. 21, 2014.

TECHNICAL FIELD

The present invention relates to a bispecific antibody with a novel format and a method for producing the same.

BACKGROUND ART

A bispecific antibody is an antibody that recognizes two different antigens and contains heavy chain variable regions and light chain variable regions of two antibodies to each antigen. Various formats (structures) are reported for the bispecific antibody (Exp. Rev. Clin. Pharmacol., Vol. 3, No. 4, p. 491, 2010). For example, (1) a tetravalent bispecific antibody in which the carboxy terminus (C terminus) of a heavy chain variable region and a light chain variable region of one antibody are respectively linked to the amino terminus (N terminus) side of a heavy chain and a light chain of the other antibody via linkers (referred to as DVD-Ig, Patent Document 1), (2) a bivalent bispecific antibody in which a heavy chain and a light chain of each antibody are conjugated via CH3 by knobs-into-holes technology (WO1998/050431), (3) a tetravalent bispecific antibody in which the C terminus of scFv of one antibody is linked to the N terminus of a heavy chain or a light chain of the other antibody via a linker, or in which the N terminus of scFv of one antibody is linked to the C terminus of a heavy chain or a light chain of the other antibody via a linker (Nat. Biotechnol., Vol. 15, No. 2, p. 159, 1997) and the like are reported.

Among the bispecific antibody formats known up to now, in the format in which a variable region of one IgG type antibody is linked to the N terminus side of the other IgG type antibody, as in the above format of (1), an antigen binding affinity of the variable region of the linked outer side (N terminus side) of the antibody is easily maintained, and thus the format is suitable for preparing bispecific antibodies of various antibody combinations. However, in the case of the above format (1), an affinity between the variable region located on the inner side (C terminus side) and the corresponding antigen tends to decrease (Non-Patent Document 1). As one means for restoring the affinity decrease, the use of a linker having long amino acid length, and the use of a flexible linker sequence (Patent Document 1) can be mentioned. However, such a linker cannot be universally used and it is required to screen a linker that does not cause a decrease in the affinity of the inner variable region depending on the two antibodies used. Further, as other means, it is reported that the antigen binding affinity of the variable region located on the inner side is restored to some extent by enzymatic cleavage of the linker in the light chain after purification of the bispecific antibody (Non-Patent Document 1). However, it is difficult to maintain the structure between the heavy chain variable region and the light chain variable region on the outer side (N terminus side) due to the enzymatic cleavage, and the stability is decreased. Further, the linker cleavage step after antibody purification complicates a production process of the antibody and causes a decrease in amount of produced antibody.

RELATED ART

Patent Document

[Patent Document 1] WO2008/024188

Non-Patent Document

[Non-Patent Document 1] "mAbs" (USA), 2011; 3(5): 487-494

DISCLOSURE OF INVENTION

Problems to be Solved by the Invention

An object of the present invention is to provide a bispecific antibody with a novel format that retains high binding affinity to two different antigens, and can be efficiently produced in a commercial production process.

Means for Solving the Problems

The present invention may include the following inventions.

[1] A bispecific antibody comprising two heavy chains, two first light chains, and two second light chains,
wherein the heavy chains each comprise a first heavy chain variable region, a CH1 region, a first linker, a second heavy chain variable region, and a heavy chain constant region in order from the amino terminus side,
the first light chains each comprise a first light chain variable region and a first light chain constant region in order from the amino terminus side,
the second light chains each comprise a second light chain variable region and a second light chain constant region in order from the amino terminus side,
the first heavy chain variable region and the first light chain variable region form a first antigen binding site,
the second heavy chain variable region and the second light chain variable region form a second antigen binding site, and
the first antigen binding site and the second antigen binding site recognize different antigens each other.

[2] A host cell selected from the following a) to c):
a) a host cell transformed with an expression vector comprising a polynucleotide comprising a base sequence encoding the heavy chain of the bispecific antibody described in [1], and a polynucleotide comprising a base sequence encoding the first light chain and the second light chain of the bispecific antibody;
b) a host cell transformed with an expression vector comprising a polynucleotide comprising a base sequence encoding the heavy chain of the bispecific antibody described in [1], and an expression vector comprising a polynucleotide comprising a base sequence encoding the first light chain and the second light chain of the bispecific antibody; and
c) a host cell transformed with an expression vector comprising a polynucleotide comprising a base sequence encoding the heavy chain of the bispecific antibody described in [1], and a host cell transformed with an expression vector comprising a polynucleotide comprising a base sequence encoding the first light chain and the second light chain of the bispecific antibody, wherein the polynucleotide comprising the base sequence encoding the first light chain and the second light chain of the bispecific antibody comprises a base sequence encoding a polypeptide in which the amino terminus of the second light chain is linked to the carboxy terminus of the first light chain via a second linker, and the second linker is a peptide linker comprising a protease recognition sequence.

[3] The host cell described in [2], wherein the second linker is the peptide linker comprising an intracellular protease recognition sequence.

[4] A method for producing a bispecific antibody, comprising culturing the host cell described in [2], and expressing the bispecific antibody.

[5] A bispecific antibody, which can be produced by the method described in [4].

[6] A method for producing a bispecific antibody, comprising culturing the host cell described in [3], and expressing the bispecific antibody.

[7] The method described in [6], wherein the second linker is cleaved by a protease in the host cell during the culturing step.

[8] A bispecific antibody, which can be produced by the method described in [6] or [7].

[9] An antigen binding fragment of the bispecific antibody described in [1].

[10] The antigen binding fragment described in [9], which is Fab, Fab', or F(ab')$_2$.

The present invention further includes the following inventions.

[11] A bispecific antibody comprising two light chains, two fragments of a first heavy chain, and two second heavy chains, wherein the light chains each comprise a first light chain variable region, a first light chain constant region, a first linker, a second light chain variable region, and a second light chain constant region in order from the amino terminus side, the fragments of the first heavy chain each comprise a first heavy chain variable region and a CH1 region in order from the amino terminus side, the second heavy chains each comprise a second heavy chain variable region and a heavy chain constant region in order from the amino terminus side, the first heavy chain variable region and the first light chain variable region form a first antigen binding site, the second heavy chain variable region and the second light chain variable region form a second antigen binding site, and the first antigen binding site and the second antigen binding site recognize different antigens each other.

[12] A host cell selected from the following a) to c):

a) a host cell transformed with an expression vector comprising a polynucleotide comprising a base sequence encoding the light chain of the bispecific antibody described in [11], and a polynucleotide comprising a base sequence encoding the fragment of the first heavy chain and the second heavy chain of the bispecific antibody;

b) a host cell transformed with an expression vector comprising a polynucleotide comprising a base sequence encoding the light chain of the bispecific antibody described in [11], and an expression vector comprising a polynucleotide comprising a base sequence encoding the fragment of the first heavy chain and the second heavy chain of the bispecific antibody; and c) a host cell transformed with an expression vector comprising a polynucleotide comprising a base sequence encoding the light chain of the bispecific antibody described in [11], and a host cell transformed with an expression vector comprising a polynucleotide comprising a base sequence encoding the fragment of the first heavy chain and the second heavy chain of the bispecific antibody, wherein the polynucleotide comprising the base sequence encoding the fragment of the first heavy chain and the second heavy chain of the bispecific antibody comprises a base sequence encoding a polypeptide in which the amino terminus of the second heavy chain is linked to the carboxy terminus of the fragment of the first heavy chain via a second linker, and the second linker is a peptide linker comprising a protease recognition sequence.

[13] The host cell described in [12], wherein the second linker is the peptide linker comprising an intracellular protease recognition sequence.

[14] A method for producing a bispecific antibody, comprising culturing the host cell described in [12] and expressing the bispecific antibody.

[15] A bispecific antibody, which can be produced by the method described in [14].

[16] A method for producing a bispecific antibody, comprising culturing the host cell described in [13] and expressing the bispecific antibody.

[17] The method described in [16], wherein the second linker is cleaved by a protease in the host cell during the culturing step.

[18] A bispecific antibody, which can be produced by the method described in [16] or [17].

[19] An antigen binding fragment of the bispecific antibody described in [11].

[20] The antigen binding fragment described in [19], which is Fab, Fab', or F(ab')$_2$.

EFFECTS OF THE INVENTION

With the bispecific antibody with the novel format according to the present invention, it can be expected to retain high binding affinity to two different antigens, and to efficiently produce in a commercial production process.

EMBODIMENTS FOR CARRYING OUT THE INVENTION

Figure 1:
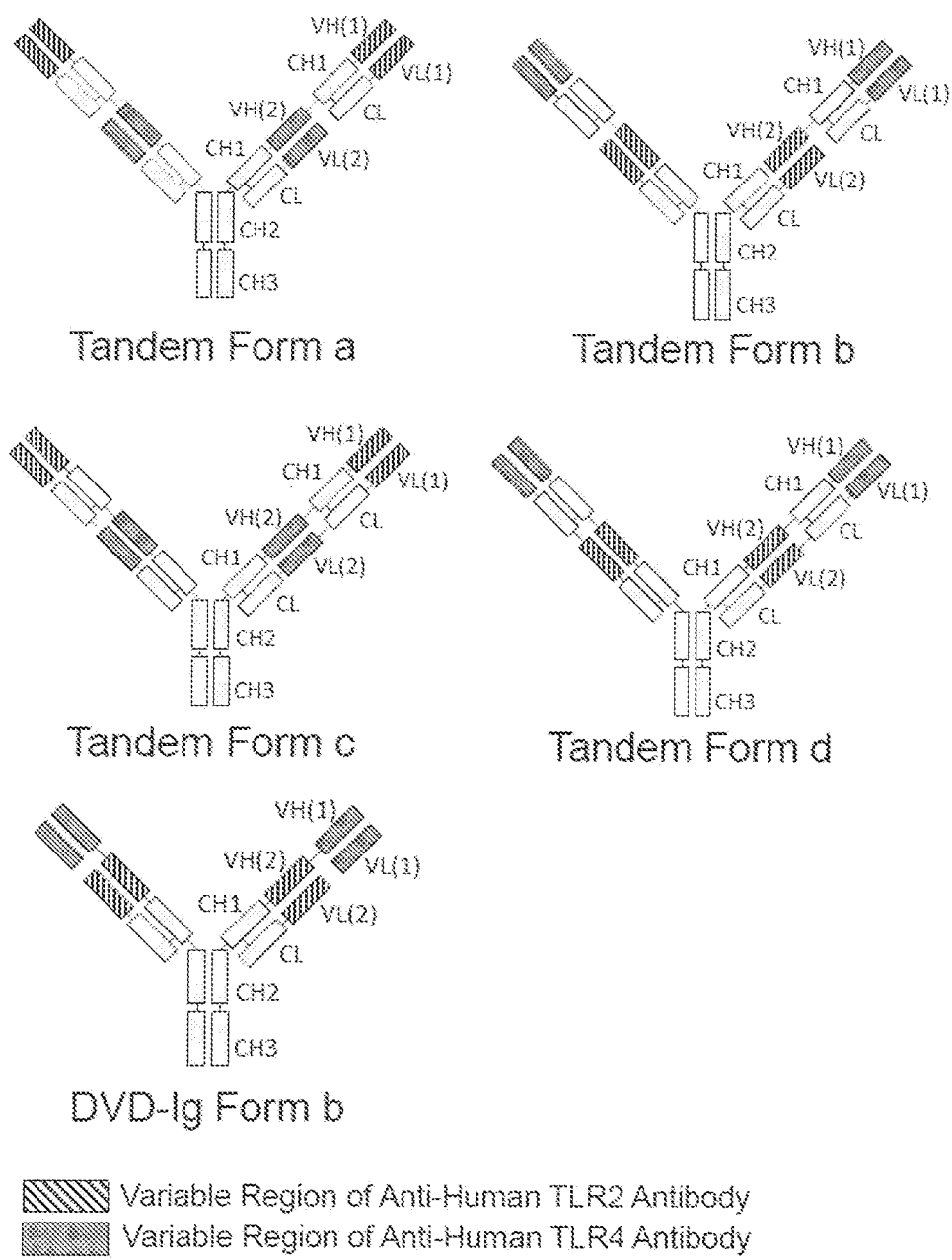
FIG. 1 shows examples of structure (tandem forms a and b) of a bispecific antibody of the present invention and examples of structure of a reference bispecific antibody (tandem form c, tandem form d, and DVD-Ig form b). In the figure, VH (1) and VL (1) represent a first heavy chain variable region and a first light chain variable region, and VH (2) and VL (2) represent a second heavy chain variable region and a second light chain variable region.

Hereinafter, the present invention will be described in detail.

With regard to antibody, there are five classes, which is IgG, IgM, IgA, IgD, and IgE. The basic structure of an antibody molecule is configured to include heavy chains having a molecular weight of 50,000 to 70,000 and light chains having a molecular weight of 20,000 to 30,000 in each of the classes in common. Heavy chain usually consists of a polypeptide chain containing approximately 440 amino acids, has a distinctive structure for each of the classes, and is referred to as Igγ, Igμ, Igα, and Igε corresponding to IgG, IgM, IgA, IgD, and IgE. Furthermore, subclasses of IgG1, IgG2, IgG3, and IgG4 are present in IgG, and the heavy chains respectively corresponding thereto are referred to as Igγ1, Igγ2, Igγ3, and Igγ4. Light chain usually consists of a polypeptide chain containing approximately 220 amino acids, two types thereof, L type and K type, are known, and are referred to as Igλ and Igκ, respectively. In a peptide configuration of the basic structure of an antibody molecule, two homologous heavy chains and two homologous light chains, are respectively bound by disulfide bonds (S—S bond) and non-covalent bonds and the molecular weight thereof is 150,000 to 190,000. The two types of light chains can be paired with any heavy chain. Individual antibody molecules normally consist of two identical light chains and two identical heavy chains.

There are four intra-chain S—S bonds in the heavy chain (five in Igμ and Igε) and two thereof in the light chain, and one loop is formed every 100 to 110 amino acid residues. This steric structure is similar between each of the loops and is referred to as a structural unit or a domain. The domain located on then amino terminus (N terminus) side in both of the heavy chain and the light chain, whose amino acid sequence is not constant even in a case of a sample from the same class (subclass) of the same kind of animal, is referred to as a variable region. Each domain is respectively referred to as a heavy chain variable region (VH) and a light chain variable region (VL). The amino acid sequence on the carboxy terminus (C terminus) side from the variable region is substantially constant in each class or subclass and is referred to as a constant region. Each domain is referred to as a heavy chain constant region (CH) and a light chain constant region (CL). The heavy chain constant region (CH) is further divided into three regions of CH1, CH2, and CH3 from an N terminus side. The region between the CH1 region and the CH2 region of the heavy chain constant region of the antibody is referred to as a hinge region and is involved in the mobility of the structure consisting of the heavy chain variable region and the CH1 region.

Bispecific Antibody of the Present Invention

Bispecific antibodies of the present invention include the bispecific antibodies described in (1) and (2) below:

(1) Heavy Chain-linked Bispecific Antibody

A bispecific antibody comprising two heavy chains, two first light chains, and two second light chains, in which the heavy chains each comprise a first heavy chain variable region, a CH1 region, a first linker, a second heavy chain variable region, and a heavy chain constant region in order from the amino terminus side, the first light chains each comprise a first light chain variable region and a first light chain constant region in order from the amino terminus side, the second light chains each comprise a second light chain variable region and a second light chain constant region in order from the amino terminus side, the first heavy chain variable region and the first light chain variable region form a first antigen binding site, the second heavy chain variable region and the second light chain variable region form a second antigen binding site, and the first antigen binding site and the second antigen binding site recognize different antigens each other.

(2) Light Chain-linked Bispecific Antibody

A bispecific antibody comprising two light chains, two fragments of a first heavy chain, and two second heavy chains, in which the light chains each comprise a first light chain variable region, a first light chain constant region, a first linker, a second light chain variable region, and a second light chain constant region in order from the amino terminus side, the fragments of the first heavy chain each comprise a first heavy chain variable region and a CH1 region in order from the amino terminus side, the second heavy chains each comprise a second heavy chain variable region and a heavy chain constant region in order from the amino terminus side, the first heavy chain variable region and the first light chain variable region form a first antigen binding site, the second heavy chain variable region and the second light chain variable region form a second antigen binding site, and the first antigen binding site and the second antigen binding site recognize different antigens each other.

In the present specification, "bispecific antibody" means an antibody that recognizes two different antigens and comprises the heavy chain variable regions and the light chain variable regions of two antibodies to each antigen. In the present specification, "antigen" means any substance (for example, protein) or a portion thereof to which an antibody binds. The combination of antigens recognized by the bispecific antibody of the present invention is not limited, and those skilled in the art can appropriately select a combination of two antibodies depending on the intended therapeutic application, for example, a combination of two antibodies against different proteins, or a combination of two antibodies binding to different portions of the same protein from each other. An example of the structure of the bispecific antibody of the present invention is shown in FIG. 1 (tandem forms a and b).

The first and second heavy chain variable regions and the first and second light chain variable regions used in the bispecific antibody of the present invention include human antibodies and humanized antibodies, but the heavy chain variable region and light chain variable region of any form of antibody which are not limited thereto can be used.

In the CH1 region, the CH1 region of the heavy chain constant region of any subclass (for example, constant region of Igγ1, Igγ2, Igγ3, or Igγ4) can be selected. In one embodiment, the CH1 region between the first heavy chain variable region and the linker in the heavy chain is the CH1 region of a human Igγ1 constant region.

The heavy chain constant region can select any subclass of the heavy chain constant region (for example, constant region of Igγ1, Igγ2, Igγ3, or Igγ4), and may be the same as or different from the subclass of the CH1 region. Preferably, the subclass of the CH1 region and the subclass of the heavy chain constant region are the same. In one embodiment, the heavy chain constant region is a human Igγ1 constant region.

The first light chain constant region and the second light chain constant region can select any subclass of the light chain constant region (for example, constant region of Igλ or Igκ), and may be the same as or different from each other. In one embodiment, the first light chain constant region and the second light chain constant region are human Igκ constant regions.

The first linker links the CH1 region and the second heavy chain variable region for the heavy chain-linked bispecific antibody, and the first light chain constant region and the second light chain variable region for the light chain-linked bispecific antibody. Any peptide (peptide linker) may be used as long as the bispecific antibody has the function thereof. The length and amino acid sequence of the first linker can be appropriately selected by those skilled in the art. Preferably, the first linker is a peptide consisting of at least 5, more preferably at least 10, and still more preferably 15 to 50 amino acids. A preferred first linker is a peptide linker comprising the amino acid sequence of GlyGlyGlyGlySer (indicated as $(Gly)_4Ser$) (referred to as GS linker), preferably comprises a plurality of pieces of $(Gly)_4Ser$, and more preferably 3 to 5 pieces of $(Gly)_4Ser$. An example of the first linker is a peptide linker consisting of the amino acid sequence of amino acid numbers 222 to 236 of SEQ ID NO: 2 (indicated as $((Gly)_4Ser)_3$).

The bispecific antibody of the present invention has binding affinity to two different antigens. Whether or not the bispecific antibody has the binding activity to each antigen can be confirmed by using the measuring methods known in the relevant field. Such measuring methods include methods such as Enzyme-Linked Immuno Sorbent Assay (ELISA), a surface plasmon resonance (SPR) analysis and the like, and are appropriately selected by those skilled in the art depending on the antigen of interest.

The present invention includes an antigen binding fragment of the bispecific antibody of the present invention. The antigen binding fragment of the bispecific antibody of the present invention comprises the first and second heavy chain variable regions and the first and second light chain variable regions, and means a fragment of a bispecific antibody having the binding activity to each of two antigens. Representative antigen binding fragment includes Fab, Fab', and $F(ab')_2$.

For the heavy chain-linked bispecific antibody, the Fab is an antigen binding fragment of the bispecific antibody comprising the heavy chain fragment consisting of a region from the first heavy chain variable region of the heavy chain to a portion of the hinge region of the heavy chain constant region, the first light chain, and the second light chain. The Fab' is an antigen binding fragment of the bispecific antibody comprising the heavy chain fragment consisting of a region from the first heavy chain variable region of the heavy chain to a portion of the hinge region of the heavy chain constant region, the first light chain, and the second light chain, in which the portion of the hinge region comprises cysteine residues which used to constitute the S—S bond between the heavy chains. The $F(ab')_2$ is an antigen binding fragment of the bispecific antibody in which two Fab's are linked by the S—S bond between the heavy chains in the hinge region.

For the light chain-linked bispecific antibody, the Fab is an antigen binding fragment of the bispecific antibody comprising the light chain (comprising from the first light chain variable region to the second light chain constant region), the fragment of the first heavy chain, and the fragment of the second heavy chain consisting of the heavy chain variable region of the second heavy chain and a CH1 region and a portion of the hinge region of the heavy chain constant region. The Fab' is an antigen binding fragment of the bispecific antibody comprising the light chain (comprising from the first light chain variable region to the second light chain constant region), the fragment of the first heavy chain, and the fragment of the second heavy chain consisting of the heavy chain variable region of the second heavy chain and a CH1 region and a portion of the hinge region of the heavy chain constant region, in which the portion of the hinge region comprises cysteine residues which used to constitute the S—S bond between the heavy chains. The $F(ab')_2$ is the antigen binding fragment of the bispecific antibody in which two Fab's are linked by the S—S bond between the heavy chains in the hinge region.

Host Cell of the Present Invention

A host cell of the present invention includes a host cell having the following characteristics:

(1) Host Cell for Preparing Heavy Chain-linked Bispecific Antibody

A host cell selected from the following a) to c):

a) a host cell transformed with an expression vector comprising a polynucleotide comprising a base sequence encoding the heavy chain of the heavy chain-linked bispecific antibody, and a polynucleotide comprising a base sequence encoding the first light chain and the second light chain of the bispecific antibody;

b) a host cell transformed with an expression vector comprising a polynucleotide comprising a base sequence encoding the heavy chain of the heavy chain-linked bispecific antibody, and an expression vector comprising a polynucleotide comprising a base sequence encoding the first light chain and the second light chain of the bispecific antibody; and c) a host cell transformed with an expression vector comprising a polynucleotide comprising a base sequence encoding the heavy chain of the heavy chain-linked bispecific antibody, and a host cell transformed with an expression vector comprising a polynucleotide comprising a base sequence encoding the first light chain and the second light chain of the bispecific antibody, in which the polynucleotide comprising the base sequence encoding the first light chain and the second light chain of the bispecific antibody comprises a base sequence encoding a polypeptide in which the amino terminus of the second light chain is linked to the carboxy terminus of the first light chain via a second linker, and the second linker is a peptide linker comprising a protease recognition sequence.

(2) Host Cell for Preparing Light Chain-linked Bispecific Antibody

A host cell selected from the following a) to c):

a) a host cell transformed with an expression vector comprising a polynucleotide comprising a base sequence encoding the light chain of the light chain-linked bispecific antibody, and a polynucleotide comprising a base sequence encoding the fragment of the first heavy chain and the second heavy chain of the bispecific antibody;

b) a host cell transformed with an expression vector comprising a polynucleotide comprising a base sequence encoding the light chain of the light chain-linked bispecific antibody, and an expression vector comprising a polynucleotide comprising a base sequence encoding the fragment of the first heavy chain and the second heavy chain of the bispecific antibody; and c) a host cell transformed with an expression vector comprising a polynucleotide comprising a base sequence encoding the light chain of the light chain-linked bispecific antibody, and a host cell transformed with an expression vector comprising a polynucleotide comprising a base sequence encoding the fragment of the first heavy chain and the second heavy chain of the bispecific antibody, in which the polynucleotide comprising a base sequence encoding the fragment of the first heavy chain and the second heavy chain of the bispecific antibody comprises a base sequence encoding a polypeptide in which the amino terminus of the second heavy chain is linked to the carboxy terminus of the fragment of the first heavy chain via a second linker, and the second linker is a peptide linker comprising a protease recognition sequence.

A cell used for preparing the host cell of the present invention is not particularly limited as long as the cell is suitable for the expression vector to be used, and is capable of expressing the bispecific antibody of the present invention by being transformed with the expression vector. Examples of the host cell include various cells such as native cells or artificially established cells which are generally used in the field of the present invention (for example, animal cells (e.g., CHO-K1SV cells), insect cells (e.g., Sf9), bacteria (e.g., *Escherichia*), yeast (e.g., *Saccharomyces* or *Pichia*)). Preferably cultured cells such as CHO-K1SV cells, CHO-DG 44 cells, 293 cells, or NS0 cells can be used.

The second linker is a peptide (peptide linker) comprising a protease recognition sequence, for the host cell for preparing the heavy chain-linked bispecific antibody, the second linker links the first light chain and the second light chain, and for the host cell for preparing the light chain-linked bispecific antibody, the second linker links the fragment of the first heavy chain and the second heavy chain. The length of the second linker can be appropriately selected by those skilled in the art, but preferably, the second linker is a peptide consisting of 5 to 60 amino acids. As the protease recognition sequence, various protease recognition sequences known in the art can be used (J. Biol. Chem., Vol. 283, No. 30, p. 20897, 2008). Preferably, the protease recognition sequence is an intracellular protease recognition sequence within the host cell. Examples of the intracellular protease recognition sequences include the amino acid sequence shown by SEQ ID NO: 5 (recognized by intracellular proteases Furin, PC 7, and PACE 4), the amino acid sequence shown by SEQ ID NO: 6 (recognized by PC 7 and PACE 4), the amino acid sequence shown by SEQ ID NO: 7 (recognized by Furin), and an amino acid sequence shown by SEQ ID NO: 8 (recognized by Furin). The second linker may be the peptide consisting of the protease recognition sequence or may comprise a further amino acid sequence on the N terminus side and/or the C terminus side of the protease recognition sequence. An example of the further amino acid sequence includes (Gly)$_4$Ser, for example, the second linker comprises one or several (Gly)$_4$Ser. An example of the second linker includes the peptide linker consisting of the amino acid sequence shown by SEQ ID NO: 9, 10, 11, or 12.

In one embodiment, the host cell of the present invention for preparing the heavy chain-linked bispecific antibody is the host cell selected from a) and b) of the above (1), in which the second linker is the peptide linker comprising the intracellular protease recognition sequence within the host cell.

In one embodiment, the host cell of the present invention for preparing the light chain-linked bispecific antibody is the host cell selected from a) and b) of the above (2), in which the second linker is the peptide linker comprising the intracellular protease recognition sequence within the host cell.

The polynucleotide comprising the base sequence encoding the heavy chain of the bispecific antibody used in the host cell for preparing the heavy chain-linked bispecific antibody, and the polynucleotide comprising the base sequence encoding the first light chain and the second light chain of the bispecific antibody, and the polynucleotide comprising the base sequence encoding the light chain of the bispecific antibody used in the host cell for preparing the light chain-linked bispecific antibody, and the polynucleotide comprising the base sequence encoding the fragment of the first heavy chain and the second heavy chain of the bispecific antibody (hereinafter, collectively referred to as "polynucleotide of the present invention") can be easily prepared by those skilled in the art using gene synthesis methods known in the art (for example, method for synthesizing antibody genes as described in WO 90/07861), according to the base sequence designed based on each of the amino acid sequences of the heavy chain and the light chain and the first and second linkers of the bispecific antibody.

The expression vector used in the host cell of the present invention is not particularly limited as long as a polynucleotide of the present invention can be expressed in various host cells of eukaryotic cells (for example, animal cells, insect cells, plant cells, and yeast) and/or prokaryotic cells (e.g., *Escherichia coli*), and the polypeptides encoded by these can be produced. Examples of the expression vector include plasmid vectors, viral vectors (e.g., adenovirus or retrovirus), and the like. For example, expression vectors such as pEE6.4, pEE12.4 (Lonza, Inc.), AG-γ1 or AG-κ (e.g., refer to WO 94/20632) can be used.

The expression vector used in the host cell of the present invention may comprise a promoter that is operably linked to the polynucleotide of the present invention. Examples of the promoter for expressing the polynucleotide with animal cells include a virus-derived promoter such as CMV, RSV, or SV40, an actin promoter, an EF (elongation factor) 1α promoter, and a heat shock promoter. Examples of promoters for expression by bacteria (for example, *Escherichia*) include a trp promoter, a lac promoter, λPL promoter, and tac promoter. Further, examples of promoters for expression by yeast include a GAL1 promoter, a GAL10 promoter, a PH05 promoter, a PGK promoter, a GAP promoter, and an ADH promoter.

In the case of using an animal cell, an insect cell, or yeast as the host cell, the expression vector of the present invention may comprise initiation codon and termination codon. In this case, the expression vector may comprise an enhancer sequence, an untranslated region on the 5' side and the 3' side of the polynucleotide of the present invention, a secretory signal sequence, a splicing junction, a polyadenylation site, or a replicable unit. When *Escherichia coli* is used as the host cell, the expression vector may comprise an initiation codon, a termination codon, a terminator region, and a replicable unit. In this case, the expression vector may comprise a selection marker (for example, tetracycline resistant gene, ampicillin resistant gene, kanamycin resistant gene, neomycin resistant gene, or dihydrofolate reductase gene) which is generally used according to the necessity.

A method of transforming the host cell with the expression vector is not particularly limited, but, for example, a calcium phosphate method or an electroporation method can be used.

Method for Producing Bispecific Antibody of the Present Invention and Bispecific Antibody Produced by the Method Methods for producing the bispecific antibody of the present invention include a method of producing the bispecific antibody comprising culturing the host cell of the present invention and expressing the bispecific antibody.

Culturing of the host cell of the present invention can be carried out by a known method. Culture conditions, for example, the temperature, pH of culture medium, and the culture time are appropriately selected. In a case where the host cell is an animal cell, examples of the culture medium include MEM culture medium supplemented with approximately 5% to 20% of fetal bovine serum (Science, Vol. 130, No. 3373, p. 432, 1959), DMEM culture medium (Virology, Vol. 8, No. 3, p. 396, 1959), and RPMI1640 culture medium (J. Am. Med. Assoc., Vol. 199, No. 8, p. 519, 1967), a 199 culture medium (Exp. Biol. Med., Vol. 73, No. 1, p. 1, 1950). The pH of the culture medium is preferably approximately 6 to 8, and the culture is generally carried out at approximately 30° C. to 40° C. for approximately 15 hours to 72 hours while air ventilating and stirring if necessary. In a case where the host cell is an insect cell, for example, Grace's culture medium supplemented with fetal bovine serum (Proc. Natl. Acad. Sci. USA, Vol. 82, No. 24, p. 8404, 1985) can be used as the culture medium. The pH of the culture medium is preferably approximately 5 to 8, and the culture is generally carried out at approximately 20° C. to 40° C. for approximately 15 hours to 100 hours while air ventilating and stirring if necessary. In a case where the host cell is *Escherichia coli* or yeast, for example, liquid culture medium supplemented with a source of nutrients is appropriate as the culture medium. It is preferable that the nutrient culture medium contain a carbon source, an inorganic nitrogen source, or an organic nitrogen source necessary for the growth of the transformed host cell. Examples of the carbon source include glucose, dextran, soluble starch, and sucrose and examples of the inorganic nitrogen source or the organic nitrogen source include ammonium salts, nitrate salts, amino acids, corn steep liquor, peptone, casein, meat extract, soybean meal, and potato extract. Other nutrients (for example, inorganic salts (for example, calcium chloride, sodium dihydrogen phosphate, and magnesium chloride), vitamins), and antibiotics (for example, tetracycline, neomycin, ampicillin, and kanamycin) may be contained as desired. The pH of the culture medium is preferably approximately 5 to 8. In a case where the host cell is *Escherichia coli*, preferred examples of the culture medium include LB culture medium and M9 culture medium (Mol. Clo., Cold Spring Harbor Laboratory, Vol. 3, A2.2). The culture is generally carried out at approximately 14° C. to 43° C. for approximately 3 hours to 24 hours while air ventilating and stirring if necessary. In a case where the host cell is yeast, as the culture medium, for example, Burkholder minimal medium (Proc. Natl. Acad, Sci, USA, Vol. 77, No. 8, p. 4505, 1980) can be used. The culture is generally carried out at approximately 20° C. to 35° C. for approximately 14 hours to 144 hours while air ventilating and stirring if necessary. By the culturing as described above, the bispecific antibody of the present invention can be expressed.

In one embodiment, the second linker in the host cell of the present invention used is the peptide linker comprising the intracellular protease recognition sequence.

In one embodiment, the host cell of the present invention used for preparing the heavy chain-linked bispecific antibody is the host cell selected from a) and b) of <Host Cell of the Present Invention>(1), in which the second linker is the peptide linker comprising the intracellular protease recognition sequence within the host cell.

In one embodiment, the host cell of the present invention used for preparing the light chain-linked bispecific antibody is the host cell selected from a) and b) of <Host Cell of the Present Invention>(2), in which the second linker is the peptide linker comprising the intracellular protease recognition sequence within the host cell.

In a preferred embodiment, the second linker in the host cell of the present invention used is the peptide linker comprising the intracellular protease recognition sequence, and the second linker is cleaved by the protease within the host cell in the culturing step.

The method of producing the bispecific antibody of the present invention may include a step of treating the bispecific antibody with the protease capable of cleaving the protease recognition sequence in the second linker, if necessary, in addition to a step of culturing the host cell of the present invention and expressing the bispecific antibody. Whether or not the protease treatment step is performed can be appropriately selected by those skilled in the art based on the protease recognition sequence to be used, the host cell, culture conditions, and the like. The protease treatment step can be performed using methods known in the art depending on the protease recognition sequence to be used. For example, the precision protease recognition sequence (SEQ ID NO: 13) may be used as the protease recognition sequence in the second linker, and a treatment with a precision protease (GE Healthcare Japan Corporation) may be performed after the culturing step.

The method of producing the bispecific antibody of the present invention may include a step of recovering, preferably isolating or purifying the bispecific antibody from the host cell, in addition to a step of culturing the host cell of the present invention and expressing the bispecific antibody. Examples of the isolation or purification method include methods using solubility such as salting-out and the solvent precipitation method, methods using the difference in molecular weight such as dialysis, ultrafiltration, and gel filtration, methods using an electric charge such as ion exchange chromatography and hydroxylapatite chromatography, methods using specific affinity such as affinity chromatography, methods using the difference in hydrophobicity such as reverse phase high performance liquid chromatography, and methods using the difference in the isoelectric point such as isoelectric focusing. Preferably, the antibody accumulated in a culture supernatant can be purified by various chromatographies, for example, column chromatography using Protein A column or Protein G column.

Bispecific antibodies of the present invention include the bispecific antibody that can be produced by the method for producing the bispecific antibody of the present invention.

The present invention has been generally described and specific examples referred to for better understanding will be provided, but these are merely examples and the present invention is not limited thereto.

Examples

With regard to parts using commercially available kits or reagents, the experiments were carried out according to the attached protocol unless specifically otherwise noted. For the sake of convenience, a concentration in mol/L is represented by M. For example, a 1 M aqueous sodium hydroxide solution means a 1 mol/L aqueous sodium hydroxide solution.

Example 1

Preparation of the Bispecific Antibody

In this example, the following two kinds of bispecific antibodies were prepared as the bispecific antibody of the present invention.

1) A bispecific antibody comprising a heavy chain in which the heavy chain variable region and the CH1 region of an anti-human TLR2 antibody are linked to the N terminus side of the heavy chain of an anti-human TLR4 antibody via a linker, the light chain of the anti-human TLR2 antibody, and the light chain of the anti-human TLR4 antibody (FIG. 1, referred to as tandem form a); and 2) A bispecific antibody in which the heavy chain variable region and the light chain variable region of the anti-human TLR2 antibody with tandem form a and the heavy chain variable region and the light chain variable region of the anti-human TLR4 antibody are respectively substituted (FIG. 1, referred to as tandem form b)

<Preparation of Tandem Form a>

A gene encoding a signal sequence (Protein., Eng., Vol. 1, No. 6, p. 499, 1987) was ligated to the 5' side of the gene encoding the heavy chain of the bispecific antibody, and the heavy chain gene was inserted into the GS vector pEE6.4 (Lonza Co., Ltd.). The base sequence of the heavy chain of the bispecific antibody is shown by SEQ ID NO: 1, and the amino acid sequence encoded thereby is shown by SEQ ID NO: 2. The region consisting of the amino acid sequence of amino acid numbers 1 to 117 of SEQ ID NO: 2 is a heavy chain variable region of the anti-human TLR2 antibody. The region consisting of the amino acid sequence of amino acid numbers 118 to 221 of SEQ ID NO: 2 is a CH1 region of a human Igγ1. The region consisting of the amino acid sequence of amino acid numbers 222 to 236 of SEQ ID NO: 2 is a linker sequence. The region consisting of the amino acid sequence of amino acid numbers 237 to 355 of SEQ ID NO: 2 is a heavy chain variable region of the anti-human TLR4 antibody. The region consisting of the amino acid sequence of amino acid numbers 356 to 685 of SEQ ID NO: 2 is a heavy chain constant region of the human Igγ1.

The gene encoding the signal sequence (Protein., Eng., Vol. 1, No. 6, p. 499, 1987) was ligated to the 5' side of a gene encoding a polypeptide in which the C terminus of the light chain of the anti-human TLR2 antibody was linked to the N terminus of the light chain of the anti-human TLR4 antibody via the linker, and this light chain polypeptide gene was inserted into the GS vector pEE 12.4 (Lonza Co., Ltd.). The base sequence of the gene encoding the light chain polypeptide is shown by SEQ ID NO: 3, and the amino acid sequence encoded thereby is shown by SEQ ID NO: 4. The region consisting of the amino acid sequence of amino acid numbers 1 to 108 of SEQ ID NO: 4 is a light chain variable region of the anti-human TLR2 antibody. The region consisting of the amino acid sequence of amino acid numbers 109 to 214 of SEQ ID NO: 4 is a constant region of a human Igκ. The region consisting of the amino acid sequence of amino acid numbers 215 to 270 of SEQ ID NO: 4 is a linker sequence (SEQ ID NO: 9). The region consisting of the amino acid sequence of amino acid numbers 271 to 378 of SEQ ID NO: 4 is a light chain variable region of the anti-human TLR4 antibody. The region consisting of the amino acid sequence of amino acid numbers 379 to 484 of SEQ ID NO: 4 is a constant region of the human Igκ.

The GS vectors described above to which the heavy chain and light chain genes of the bispecific antibody were respectively inserted was cleaved with the restriction enzyme of NotI and PvuI, ligation was performed using a ligation kit Ligation-Convenience Kit (NIPPONGENE Co., Ltd.) or a ligation reagent Ligation-high (TOYOBO Co., Ltd.), and the GS vector to which both heavy chain and light chain genes were inserted is constructed. The vector for expression of both the heavy chain and light chain were transfected into Expi 293 cells (Life Technologies Co., Ltd.) cultured at approximately 3×10$^6$ cells/mL in Expi 293 Expression medium (Life Technologies Co., Ltd.) using transfection reagent ExpiFectamine 293 (Life Technologies Co., Ltd.) and cultured for 7 days. The culture supernatant was purified using Protein A or Protein G column (GE Healthcare Japan Corporation) to obtain purified antibody.

<Preparation of Tandem Form b>

A heavy chain gene having a base sequence in which the portion encoding the heavy chain variable region of the anti-human TLR2 antibody (base numbers 1 to 351 of SEQ ID NO: 1) and the heavy chain variable region of the anti-human TLR4 antibody (base numbers 709 to 1065 of SEQ ID NO: 1) were substituted in the base sequence shown by SEQ ID NO: 1 was prepared, and a GS vector of the heavy chain was prepared in the same manner as the heavy chain vector of tandem form a. A light chain polypeptide gene having a base sequence in which the portion encoding the light chain of the anti-human TLR2 antibody (base numbers 1 to 324 of SEQ ID NO: 3) and the portion encoding the light chain of the anti-human TLR4 antibody (base numbers 811 to 1134 of SEQ ID NO: 3) were substituted in the base sequence shown by SEQ ID NO: 3 was prepared, and a GS vector of the light chain polypeptide was prepared in the same manner as the light chain polypeptide vector of tandem form a. Using both GS vectors, bispecific antibodies were expressed in the same manner as the tandem form a to obtain purified antibody of tandem form b.

<Preparation of Tandem Form c>

A reference bispecific antibody (referred to as tandem form c) was prepared using a method in the same manner as the tandem form a except that, the light chain polypeptide in which the linker sequence (consisting of the amino acid sequence of amino acid numbers 215 to 270 of SEQ ID NO: 4) in the light chain polypeptide consisting of the amino acid sequence of SEQ ID NO: 4 was substituted with ((Gly)$_4$Ser)$_3$ was used.

Figure 2:
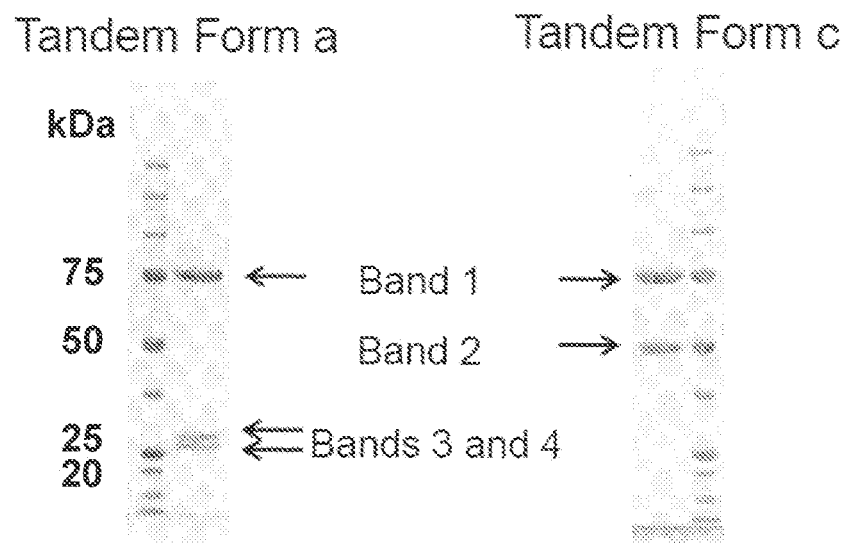
FIG. 2 shows the results of reducing SDS-PAGE analysis of tandem forms a and c. In the figure, band 1 represents a heavy chain, and band 2 represents an uncleaved light chain (light chain fragment), and bands 3 and 4 represent each of the light chains generated by linker cleavage with protease.

The results of reducing SDS-PAGE of the purified antibodies of tandem forms a and c are shown in FIG. 2. For the tandem form a, the light chain polypeptide was cleaved by intracellular protease and divided into the light chain of anti-human TLR2 antibody and the light chain of anti-human TLR4 antibody (bands 3 and 4 in FIG. 2). On the other hand, the tandem form c was expressed in a state where both light chains were linked, since the linker between the light chains does not comprise a protease recognition site (band 2 in FIG. 2).

<Preparation of Tandem Form d>

A reference bispecific antibody (referred to as tandem form d) was prepared using a method in the same manner as the tandem form b except that the light chain polypeptide in which the linker sequence (consisting of the amino acid sequence of SEQ ID NO: 9) in the light chain polypeptide of the tandem form b was substituted with ((Gly)$_4$Ser)$_3$ was used.

Reference Example

Preparation of Reference Antibody

<DVD-Ig Form b>

As a reference antibody, a bispecific antibody of DVD-Ig type (referred to as DVD-Ig form b) was prepared. As variable regions of the anti-human TLR4 antibody portion and the anti-human TLR2 antibody portion in the bispecific antibody, the same variable regions as each of the variable regions used in the tandem form b was used, and as constant regions of the heavy chain and the light chain, a human Igγ1 constant region and a human I$_D$(constant region were respectively used. As the culture and purification method, the same method as the tandem form b was used to obtain each purified antibody.

According to the method described in the document (Non-Patent Document 1), a bispecific antibody of the DVD-Ig type in which the heavy chain variable region and the light chain variable region of the anti-human TLR4 antibody were respectively linked to the N terminus of the heavy chain and the light chain of the anti-human TLR2 antibody via the linker was prepared (FIG. 1, referred to as DVD-Ig form b). As a linker of the heavy chain, the same linker as the linker used for the heavy chain of tandem form a was used. As a linker of the light chain, a linker consisting of the amino acid sequence shown by SEQ ID NO: 13 which is a precision protease recognition sequence was used. The purified antibody was subjected to enzyme treatment with a protease reaction solution (50 mM Tris-HCl, 150 mM NaCl, 1 mM EDTA, Precision Protease (GE Healthcare Japan Corporation) 5 units). After the enzyme treatment, the protease was removed with Glutathione Sepharose carrier (GE Healthcare Japan Corporation) and used in Example 10.

<Preparation of Antibody of IgG Type>

As the reference antibody, the following anti-human TLR2 antibody of IgG type (referred to as TLR2-IgG) and anti-human TLR4 antibody (referred to as TLR4-IgG) were prepared.

TLR2-IgG: an IgG antibody comprising a heavy chain comprising the heavy chain variable region and the human Igγ1 constant region of the anti-human TLR2 antibody used in tandem form a, and a light chain comprising the light chain variable region of the anti-human TLR2 antibody and the human Igκ constant region used in tandem form a.

TLR4-IgG: an IgG antibody comprising a heavy chain comprising the heavy chain variable region and the human Igγ1 constant region of the anti-human TLR4 antibody used in tandem form a, and a light chain comprising the light chain variable region of the anti-human TLR4 antibody and the human Igκ constant region used in tandem form a.

Similarly to the tandem form a, a GS vector to which the heavy chain and the light chain of each antibody were inserted was prepared, and the vector for expression of both the heavy chain and light chain was constructed from each of the GS vectors. As the culture and purification method, the same method as the tandem form a was used to obtain each of the purified antibodies.

Example 2

Evaluation of Binding Activity to Human TLR4-Tandem Form a

In order to evaluate the binding activity of the tandem form a (bispecific antibody format having the anti-human TLR2 antibody portion on the outer side and the anti-human TLR4 antibody portion on the inner side) prepared in Example 1 to the human TLR4, cell ELISA was performed. As reference antibodies, the tandem form c and the TLR4-IgG were used. Human TLR4/MD2 expressing HEK 293 cells were seeded at $1 \times 10^4$ cells/well in a BD Bio Coat poly D-lysine 384 well plate (Becton Dickinson Co., Ltd.) using an α-MEM culture medium (Life Technologies Co., Ltd.) and incubated overnight. The culture medium was discarded on the next day and 30 μL of a diluted antibody solution (tandem forms a and c are in the concentration range of final concentration from 100 nM to 0.00005 nM, and TLR4-IgG is in the concentration range of final concentration from 99 nM to 0.00005 nM, ten-step, five-fold serial dilution, respectively) of each purified antibody (tandem form a, tandem form c, or TLR4-IgG) diluted with dilution solution (Hank's buffered salt solution containing 1% bovine serum-derived albumin (BSA) and 10 mM of 2-[4-(2-hydroxyethyl)-1-piperazinyl]-ethanesulfonic acid (HEPES)) was added. After culturing at 37° C. for one hour, the cells were cleaned with a cleaning solution (Hank's buffered salt solution containing 0.1% BSA and 10 mM of HEPES) and horseradish peroxidase-labeled anti-human IgG antibody (DAKO Co., Ltd.) diluted 5000 times with the cleaning solution was added. After incubating at 37° C. for one hour, the cells were cleaned with the cleaning solution, and 25 μL of a coloring reagent TMB (MOSS Co., Ltd.) was added. Twenty minutes later, 25 μL of 1 M sulfuric acid was added to stop the color reaction, and the color intensity thereof was measured with Safire II (Tecan Co., Ltd.) to evaluate the binding activity of the antibody. Using the obtained measurement results, 50% effective concentration ($EC_{50}$) of each antibody was calculated from 4 parameter logistic curve regression by statistical analysis software GraphPad Prism (GraphPad Software Co., Ltd.).

The results are shown in Table 1. Compared to tandem form c, it was revealed that in the tandem form a in which the linker between the light chains was cleaved, the antigen binding affinity of the inner anti-human TLR4 antibody portion was increased. This result shows that the antigen binding affinity of the inner variable region was restored in the bispecific antibody of the present invention.

TABLE 1

| Binding Activity to Human TLR4 | |
| --- | --- |
| Antibody | $EC_{50}$ (M) |
| Tandem form a | $4.29 \times 10^{-9}$ |
| Tandem form c | $38.53 \times 10^{-9}$ |
| TLR4-IgG | $0.38 \times 10^{-9}$ |

Example 3

Evaluation of Binding Activity to Human TLR2—Tandem Form a

In order to evaluate the binding activity of the tandem form a prepared in Example 1 to the human TLR2, SPR analysis was performed. The tandem form c and the TLR2-IgG were used as the reference antibody. For SPR analysis, Biacore T200 (GE Healthcare Japan Corporation) was used. Anti-His IgG (attached to His Capture Kit) was immobilized on CMS sensor chip using His Capture Kit (GE Healthcare Japan Corporation, 28-9950-56) and Amine Coupling Kit (GE Healthcare Japan Corporation, BR-1000-50). Using the flow path No. 1 as a reference, the human TLR2 proteins (R&D systems Co., 2616 TR/CF) diluted to 0.66 μg/mL with HBS-EP+buffer (GE Healthcare Japan Corporation, BR-1006-69) were added at a flow rate of 5 μL/min for 2 minutes to be immobilized in the other flow path (No. 2), without immobilized human TLR2 proteins to the flow path No. 1. Thereafter, a solution (eight step, two fold serial dilution in the concentration range of final concentration from 100 nM to 0.781 nM) obtained by serially diluting each purified antibody (tandem form a, tandem form c, or TLR 2-IgG) with HBS-EP+buffer was added at a flow rate of 50 μL/min for 2 minutes, and the binding between the purified antibody and TLR 2 was measured. Next, HBS-EP+buffer was added at a flow rate of 50 μL/min for 5 minutes, and dissociation of the purified antibody and the human TLR2 was measured. Bivalent analyte model, Rmax was analyzed by Fit local, a binding rate constant ($k_a$) and a dissociation rate constant ($k_d$) were calculated, and $k_d$ was divided by $k_a$ to calculate the binding dissociation constant ($K_D$).

The results are shown in Table 2. It was revealed that the tandem form a in which the linker between the light chains was cleaved maintained the antigen binding affinity of the outer anti-human TLR2 antibody portion. This result shows that in the bispecific antibody of the present invention, cleavage of the linker between the light chains does not affect the antigen binding affinity of the outer variable region.

TABLE 2

| Binding Activity to Human TLR2 | |
|---|---|
| Antibody | $K_D$ (M) |
| Tandem form a | $2.32 \times 10^{-9}$ |
| Tandem form c | $2.56 \times 10^{-9}$ |
| TLR2-IgG | $2.69 \times 10^{-9}$ |

Example 4

Preparation of Antibody using Various Expressing Cells—Tandem Form a

In preparation of the tandem form a of Example 1, the tandem form a was prepared by expressing in CHO-K1SV cells instead of Expi 293 cells. Specifically, CHO-K1SV cells (Lonza Co., Ltd) cultured at approximately $1 \times 10^7$ cells/mL in CD-CHO medium (Life Technologies, Inc.) were transfected with the vector for expression of both the heavy chain and the light chain of tandem form a described in Example 1 by an electroporation method, and cultured for 7 days. The culture supernatant was purified using protein A or protein G column (GE Healthcare Japan Corporation) to obtain a purified antibody.

For the tandem form a expressed in Expi 293 cells and CHO-K1SV cells, the binding activity to the human TLR4 was evaluated using the method described in Example 2. As a dilution series of the purified antibody, the tandem form a expressed in Expi 293 cells was evaluated in the concentration range of 42 nM to 0.00002 nM, and the tandem form a expressed in CHO-K1SV cells was evaluated in the concentration range of final concentration from 35 nM to 0.00002 nM, respectively.

The results are shown in Table 3. It was revealed that the antigen binding activity of the inner anti-human TLR4 antibody portion was maintained even in a case of expression in any cell lines.

TABLE 3

| Binding Activity to Human TLR4 | |
|---|---|
| Antibody (Expressing cells) | $EC_{50}$ (M) |
| Tandem form a (Expi 293 cells) | $4.94 \times 10^{-9}$ |
| Tandem form a (CHO-K1SV cells) | $4.17 \times 10^{-9}$ |

Example 5

Evaluation of Neutralization Activity to Human TLR4—Tandem Form a

In order to evaluate the neutralization activity of the tandem form a prepared in Example 4 to the human TLR4, IL-6 production inhibition assay induced by lipopolysaccharide (LPS) as a TLR4 ligand was performed using U937 cells, which is human monocytic lineage cells that endogenously express the human TLR4/MD2. As a reference antibody, tandem form c and TLR4-IgG were used.

U937 cells (ATCC: CRL-1593.2) were seeded two days before the experiment in a 384 well plate (Thermo Scientific Co., Ltd.) at 30 μL/well under a RPMI 1640 culture medium (Life Technologies, Inc.) so as to be $2 \times 10^4$ cells/well. At that time, PMA (Phorbol ester (Funakoshi Co., Ltd., PE-160)) was added to the culture medium to the final concentration of 100 nM. On the next day, 10 μL of diluted solution (ten-step, five fold serial dilution in the concentration range of final concentration from 20 nM to 0.00001 nM) of each purified antibody (tandem form a, tandem form c, or TLR4-IgG) diluted in the culture medium was added, and the cells were incubated at 37° C. under 5% $CO_2$ for 30 minutes. Furthermore, 10 μL of LPS (Alexis Co., Ltd.; final concentration 100 ng/mL) diluted in the culture medium was added, and the cells were cultured overnight at 37° C. under 5% $CO_2$ condition. On the next day, the culture supernatant was collected and the concentration of the human IL-6 contained in the culture supernatant was measured with EnVision (registered trademark) (Perkin Elmer Co.) using a commercially available AlphaLISA (registered trademark) kit (Thermo Scientific Co., Ltd.). Using the obtained measurement results, the 50% inhibitory concentration ($IC_{50}$) of each antibody was calculated from 4-parameter logistic curve regression by statistical analysis software GraphPad Prism (GraphPad Software Co., Ltd.).

The results are shown in Table 4. Compared to tandem form c, it was revealed that the neutralization activity of the inner anti-human TLR4 antibody portion was restored in the tandem form a in which the linker between the light chains was cleaved.

TABLE 4

| Neutralization Activity to Human TLR4 | |
|---|---|
| Antibody | $IC_{50}$ (M) |
| Tandem form a | $0.51 \times 10^{-11}$ |
| Tandem form c | $3.52 \times 10^{-11}$ |
| TLR4-IgG | $0.22 \times 10^{-11}$ |

Example 6

Evaluation of Neutralization Activity to Human TLR2—Tandem Form a

In order to evaluate the neutralization activity of the tandem form a prepared in Example 4 to the human TLR2, IL-6 production inhibition assay induced by Pam2CSK4 as a TLR2 ligand was performed using U937 cells, which is human monocytic lineage cells that endogenously express the human TLR2. As a reference antibodies, tandem form c and TLR2-IgG were used.

U937 cells (ATCC: CRL-1593.2) were seeded two days before the experiment in a 384 well plate (Thermo Scientific Co., Ltd.) at 30 µL/well under a RPMI 1640 culture medium (Life Technologies, Inc.) at 2×10$^4$ cells/well. At that time, PMA (Phorbol ester (Funakoshi Co., Ltd., PE-160)) was added to the culture medium to the final concentration of 100 nM. On the next day, 10 µL of diluted solution (tandem forms a and c were in the concentration range of final concentration from 20 nM to 0.00001 nM, and TLR2-IgG was in the concentration range of final concentration from 19 nM to 0.00001 nM, ten-step, five fold serial dilution, respectively) of each purified antibody (tandem form a, tandem form c, or TLR2-IgG) diluted in the culture medium was added, and the cells were incubated at 37° C. under 5% $CO_2$ condition for 30 minutes. Furthermore, 104 of Pam2CSK4 (Invivogen Co., Ltd., tlrl-pm2s; final concentration 10 ng/mL) diluted in the culture medium was added, and the cells were cultured overnight at 37° C. under 5% $CO_2$ condition. On the next day, the culture supernatant was collected and the concentration of the human IL-6 contained in the culture supernatant was measured with EnVision (registered trademark) (Perkin Elmer Co.) using a commercially available AlphaLISA (registered trademark) kit (Thermo Scientific Co., Ltd.). The 50% inhibitory concentration ($IC_{50}$) of each antibody was calculated by the method shown in Example 5.

The results are shown in Table 5. It was revealed that the tandem form a in which the linker between the light chains was cleaved maintained the neutralization activity of the outer anti-human TLR2 antibody portion.

TABLE 5

| Neutralization Activity to Human TLR2 | |
|---|---|
| Antibody | $IC_{50}$ (M) |
| Tandem form a | $0.25 \times 10^{-9}$ |
| Tandem form c | $0.21 \times 10^{-9}$ |
| TLR2-IgG | $0.09 \times 10^{-9}$ |

Example 7

Preparation of Antibody using Various Protease Recognition Sequences and Evaluation of Binding Activity—Tandem Form a In the preparation of the tandem form a of Examples 1 and 4, the tandem form a was prepared, using three kinds of linkers (SEQ ID NO: 10, SEQ ID NO: 11, and SEQ ID NO: 12, respectively) in which the protease recognition sequence (SEQ ID NO: 5) in the linker of the light chain polypeptide was substituted with various intracellular protease recognition sequences (SEQ ID NO: 6, SEQ ID NO: 7, and SEQ ID NO: 8). SDS-PAGE was performed on the tandem form a prepared in this example. Furthermore, the binding activity to the human TLR4 was evaluated using the method described in Example 2. Dilution series of each purified antibody were evaluated in a concentration range of 42 nM to 0.00002 nM.

Figure 3:
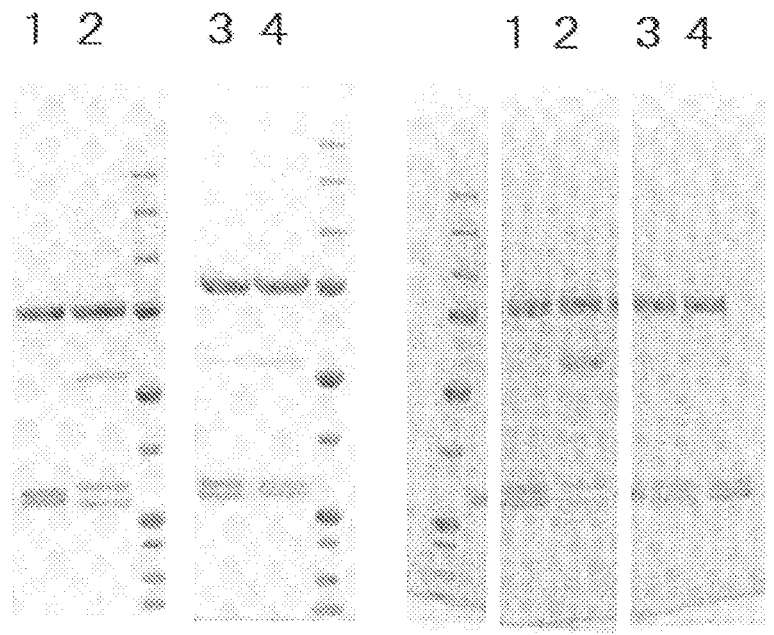
FIG. 3 shows the results of reducing SDS-PAGE analysis of tandem form a having various protease recognition sequences. The left is the analysis result of antibodies expressed in Expi 293 cells and the right is the analysis result of antibodies expressed in CHO-K1SV cells. Lanes 1, 2, 3, and 4 are the results of tandem form a expressed using a linker comprising protease recognition sequences of SEQ ID NOs: 5, 6, 7 and 8, respectively.

The results of reducing SDS-PAGE are shown in FIG. 3. For any bispecific antibody, the linker of the light chain polypeptide was cleaved by intracellular protease in a case of being expressed in Expi 293 cells and CHO-K1SV cells, and divided into the light chain of the anti-human TLR2 antibody and the light chain of the anti-human TLR4 antibody.

The results of the binding activity of each antibody expressed in Expi 293 cells to the human TLR4 are shown in Table 6. Even in a case where any protease recognition sequence was used as a linker between light chains, the antigen binding activity of the inner anti-human TLR4 antibody portion was maintained.

TABLE 6

| Binding Affinity to Human TLR4 | |
|---|---|
| Antibody (Protease Recognition Sequence) | $EC_{50}$ (M) |
| Tandem form a (SEQ ID NO: 5) | $3.53 \times 10^{-9}$ |
| Tandem form a (SEQ ID NO: 6) | $2.82 \times 10^{-9}$ |
| Tandem form a (SEQ ID NO: 7) | $3.33 \times 10^{-9}$ |
| Tandem form a (SEQ ID NO: 8) | $4.24 \times 10^{-9}$ |

Example 8

Evaluation of Neutralization Activity to Human TLR4—Tandem Form b

In order to evaluate the neutralization activity of the tandem form b (bispecific antibody format having the anti-human TLR4 antibody portion on the outer side and the anti-human TLR2 antibody portion on the inner side) prepared in Example 1 to the human TLR4, the LPS-induced IL-6 production inhibition assay used in Example 5 was performed. As a test antibody, in the preparation of the tandem form b of Example 1, the tandem form b prepared with CHO-K1SV cells was used, using three kinds of linkers (SEQ ID NO: 10, SEQ ID NO: 11, and SEQ ID NO: 12, respectively) in which the protease recognition sequence (SEQ ID NO: 5) in the linker of the light chain polypeptide was substituted with various intracellular protease recognition sequences (SEQ ID NO: 6, SEQ ID NO: 7, and SEQ ID NO: 8). As the reference antibodies, the tandem form d and the TLR4-IgG were used. With respect to the final concentration of the test antibody, the test was performed in the concentration range of final concentration from 20 nM to 0.00001 nM, respectively.

The results are shown in Table 7. The tandem form b in which the linker between the light chains was cleaved maintained the neutralization activity of the outer anti-human TLR4 antibody portion. The results of Example 6 and this Example show that in the bispecific antibody of the present invention, cleavage of the linker between light chains does not affect the neutralization activity of the outer variable region.

TABLE 7

| Neutralization Activity to Human TLR4 | |
|---|---|
| Antibody (Protease Recognition Sequence) | $IC_{50}$ (M) |
| Tandem form b (SEQ ID NO: 5) | $0.48 \times 10^{-11}$ |
| Tandem form b (SEQ ID NO: 6) | $0.59 \times 10^{-11}$ |
| Tandem form b (SEQ ID NO: 7) | $0.55 \times 10^{-11}$ |
| Tandem form b (SEQ ID NO: 8) | $0.53 \times 10^{-11}$ |
| Tandem form d | $0.49 \times 10^{-11}$ |
| TLR4-IgG | $0.22 \times 10^{-11}$ |

Example 9

Evaluation of Neutralization Activity to Human TLR2—Tandem Form b

In order to evaluate the neutralization activity of the tandem form b prepared in Example 8 to the human TLR2, IL-6 production inhibition assay induced by Pam2CSK4 used in Example 6 was performed. As the reference antibodies, the tandem form d and the TLR2-IgG were used. With respect to the final concentration of the test antibody, for the tandem form b and the tandem form d, the test was performed in the concentration range of final concentration from 20 nM to 0.00001 nM, and for TLR 2-IgG the test was performed in the concentration range of final concentration from 19 nM to 0.00001 nM, respectively.

Figure 4:
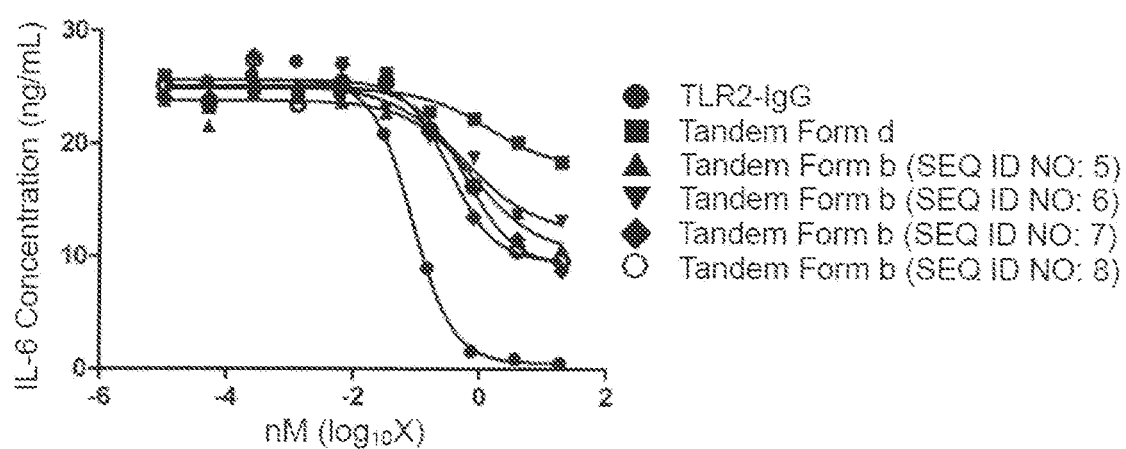
FIG. 4 shows the results of a neutralization activity evaluation of tandem form b for human TLR2.

The results are shown in FIG. 4. Compared to tandem form d, it was revealed that the neutralization activity of the inner anti-human TLR2 antibody portion was restored in the tandem form b in which the linker between the light chains is cleaved. The results of Example 5 and this Example show that the neutralization activity of the inner variable region in the bispecific antibody of the present invention was improved, compared to the bispecific antibody to which the linker between the heavy chain and the light chain is linked.

Example 10

Structural Stability of Bispecific Antibody

In order to evaluate the structural stability in the variable region of the bispecific antibody of the present invention, heat denaturation intermediate temperature (Tm value) was evaluated by Differential Scanning calorimetry (DSC). Purified antibody of tandem form b and DVD-Ig form b was buffer-substituted with a solution of 20 mM citric acid and 120 mM NaCl (pH 6.0) using a concentrated cassette Vivapore 5 (Sartorius AG Co., Ltd). For each obtained antibody solution, DSC measurement was carried out using a MicroCal VP-Capillary DSC (GE Healthcare Japan Corporation) at a rate of temperature increase of 1° C./min from 25° C. to 100° C. with a protein of approximately 0.12 mg/mL. From a degeneration curve of the obtained DSC, the Tm value of the variable region of each antibody was calculated using analysis software Origin 7 (OriginLab Co., Ltd.).

The results are shown in Table 8. In the table, Onset shows the collapse starting temperature of the antibody molecular structure. Tm1 represents a Tm value confirmed only for the DVD-Ig form b, and is attributed to the structural change of the first variable region (VH(1) and VL(1)) of the DVD-Ig form b. Tm2 of the tandem form b represents a Tm value caused by the change of the structure including the first variable region, the CH1 region and CL region on the C terminus side of the first variable region, the second variable region (VH(2) and VL(2)), the CH1 region and CL region on the C terminus side of the second variable region, and the CH2 region. Tm2 of the DVD-Ig Form b represents a Tm value attributed to the change of the structure including the second variable region, the CH1 region and CL region on the C terminus side of the second variable region, and the CH2 region. Tm 3 represents a Tm value attributed to the change of the structure in the CH3 region of each antibody. In the DVD-Ig form b, structural change of the variable region occurs at a low temperature and the DVD-Ig form b is structurally unstable, whereas tandem Form b is stable at higher temperature. Therefore, it was revealed that the bispecific antibody of the present invention is more stable to heat than the DVD-Ig type bispecific antibody.

TABLE 8

Test Results of DSC

| | Onset (° C.) | Tm1 (° C.) | Tm2 (° C.) | Tm3 (° C.) |
|---|---|---|---|---|
| Tandem Form b | 62.1 | — | 78.4 | 83.0 |
| DVD-Ig Form b | 52.9 | 62.4 | 74.4 | 83.5 |

INDUSTRIAL APPLICABILITY

The bispecific antibody with the novel format of the present invention maintains high binding affinity to both antigens, and is expected to be efficiently produced in the commercial production process. For example, the bispecific antibody is useful for research and development and commercial production of bispecific antibodies for various treatments.

SEQUENCE LIST FREE TEXT

In the number heading <223>of the sequence list below, description of "Artificial Sequence" is made. Specifically, the base sequence shown by SEQ ID NO: 1 in the sequence list is the base sequence of the heavy chain of tandem form a and the amino acid sequence shown by SEQ ID NO: 2 is the amino acid sequence of amino acid sequence encoded by SEQ ID NO: 1. The base sequence shown by SEQ ID NO: 3 in the sequence list is the base sequence of the light chain fragment of tandem form a, and the amino acid sequence shown by SEQ ID NO: 4 is the amino acid sequence encoded by SEQ ID NO: 3. The amino acid sequences shown by SEQ ID NOs: 5, 6, 7, and 8 are the protease recognition sequences. The amino acid sequences shown by SEQ ID NOs: 9, 10, 11, and 12 in the sequence list are the linker sequences in the light chain polypeptide. The amino acid sequence shown by SEQ ID NO: 13 in the sequence list is the precision protease recognition sequence.

The invention claimed is:

1. A host cell selected from the group consisting of a) and b):
  a) a host cell transformed with an expression vector comprising (i) a first polynucleotide encoding a heavy chain of a bispecific antibody, and (ii) a second polynucleotide encoding a first light chain of the bispecific antibody, a second light chain of the bispecific antibody, and a peptide linker comprising an intracellular protease recognition sequence recognized by a protease within the host cell that connects the first light chain and the second light chain and which is cleaved by a protease in the host cell during culturing of the host cell; and
  b) a host cell transformed with a first expression vector comprising a polynucleotide encoding a heavy chain of a bispecific antibody, and a second expression vector comprising a polynucleotide encoding a first light chain of the bispecific antibody, a second light chain of the bispecific antibody, and a peptide linker comprising an intracellular protease recognition sequence that connects the first light chain and the second light chain and which is cleaved by a protease in the host cell during culturing of the host cell;
  wherein the bispecific antibody comprises two heavy chains, two first light chains, and two second light chains,
  wherein each heavy chain comprises a first heavy chain variable region, a CH1 region, a linker, a second heavy chain variable region, and a heavy chain constant region,
  each first light chain comprises a first light chain variable region and a first light chain constant region,
  each second light chain comprises a second light chain variable region and a second light chain constant region; and
  wherein the first heavy chain variable region and the first light chain variable region form a first antigen binding site,
  the second heavy chain variable region and the second light chain variable region form a second antigen binding site, and
  the first antigen binding site and the second antigen binding site recognize different antigens;
  and wherein the host cell is a mammalian cell.

2. A method for producing a bispecific antibody, comprising culturing the host cell according to claim 1, and expressing the bispecific antibody.

3. The host cell according to claim 1, wherein the host cell is transformed with an expression vector comprising a polynucleotide comprising a base sequence encoding a heavy chain of a bispecific antibody, and a polynucleotide comprising a base sequence encoding a first light chain, a base sequence encoding a second light chain of the bispecific antibody, and a base sequence encoding a peptide linker comprising an intracellular protease recognition sequence that connects the first light chain and the second light chain.

4. The host cell according to claim 1, wherein the host cell is transformed with a first expression vector comprising a polynucleotide comprising a base sequence encoding a heavy chain of a bispecific antibody, and a second expression vector comprising a polynucleotide comprising a base sequence encoding a first light chain, a base sequence encoding a second light chain of the bispecific antibody, and a base sequence encoding a peptide linker comprising an intracellular protease recognition sequence that connects the first light chain and the second light chain.

* * * * *

SEQUENCE LISTING

```
<160> NUMBER OF SEQ ID NOS: 13

<210> SEQ ID NO 1
<211> LENGTH: 2055
<212> TYPE: DNA
<213> ORGANISM: Artificial Sequence
<220> FEATURE:
<223> OTHER INFORMATION: H-chain gene of tandem form a
<220> FEATURE:
```

<221> NAME/KEY: CDS
<222> LOCATION: (1)..(2055)

<400> SEQUENCE: 1

```
cag gtg cag ctg cag gag tcg ggc ccg gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc agt agt ttc      96
Thr Leu Ser Leu Thr Cys Thr Val Ser Gly Gly Ser Ile Ser Ser Phe
            20                  25                  30 tac tgg acc tgg atc agg cag ccc cca ggg aag gga ctg gag tgg att     144
Tyr Trp Thr Trp Ile Arg Gln Pro Pro Gly Lys Gly Leu Glu Trp Ile
        35                  40                  45 ggt tat att cac tac agt ggg agc acc aac tac aac ccc tcc ctc aag     192
Gly Tyr Ile His Tyr Ser Gly Ser Thr Asn Tyr Asn Pro Ser Leu Lys
    50                  55                  60 agt cga gtc acc ata tca gta gac acg tcc aag aac cag ttc tcc ctg     240
Ser Arg Val Thr Ile Ser Val Asp Thr Ser Lys Asn Gln Phe Ser Leu
65                  70                  75                  80 acg ctg agc tct gtg acc gcc gca gac acg gcc gtg tat tat tgt gcg     288
Thr Leu Ser Ser Val Thr Ala Ala Asp Thr Ala Val Tyr Tyr Cys Ala
                85                  90                  95 aga cgt agg tca atg aac tgg ttc gac ccc tgg ggc cag gga acc ctg     336
Arg Arg Arg Ser Met Asn Trp Phe Asp Pro Trp Gly Gln Gly Thr Leu
            100                 105                 110 gtc atc gtc tcc tca gcc tcc acc aag ggc cca tcg gtc ttc ccc ctg     384
Val Ile Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc     432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca     480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc     528
Gly Ala Leu Thr Ser Gly Val His Thr Phe Pro Ala Val Leu Gln Ser
                165                 170                 175 tca gga ctc tac tcc ctt agt agc gtg gtg acc gtg ccc tcc agc agc     576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac     624
Leu Gly Thr Gln Thr Tyr Ile Cys Asn Val Asn His Lys Pro Ser Asn
        195                 200                 205 acc aag gtg gac aag aaa gtt gag ccc aaa tct tgt gac ggt ggc ggt     672
Thr Lys Val Asp Lys Lys Val Glu Pro Lys Ser Cys Asp Gly Gly Gly
    210                 215                 220 ggc tct ggc ggt ggt ggg tct ggt ggc ggc gga tct gaa gtg cag ctg     720
Gly Ser Gly Gly Gly Gly Ser Gly Gly Gly Gly Ser Glu Val Gln Leu
225                 230                 235                 240 gtg gag tct ggg gga ggc ctg gtg cag cct ggc ggc tcc ctg aga ctg     768
Val Glu Ser Gly Gly Gly Leu Val Gln Pro Gly Gly Ser Leu Arg Leu
                245                 250                 255 tcc tgt gca gcc tct gga ttc acc ttt gat act tat gcc atg cac tgg     816
Ser Cys Ala Ala Ser Gly Phe Thr Phe Asp Thr Tyr Ala Met His Trp
            260                 265                 270 gtc cgg cag gct cca ggg aag ggc ctg gag tgg gtc gcc ggt att agt     864
Val Arg Gln Ala Pro Gly Lys Gly Leu Glu Trp Val Ala Gly Ile Ser
        275                 280                 285 tgg aat agt ggt aac atc ggc tat gcc gac tct gtg aag ggc cga ttc     912
Trp Asn Ser Gly Asn Ile Gly Tyr Ala Asp Ser Val Lys Gly Arg Phe
```

```
                  290                 295                 300
acc atc tcc aga gac aac tcc aag aac acc ctg tac ctg cag atg aac     960
Thr Ile Ser Arg Asp Asn Ser Lys Asn Thr Leu Tyr Leu Gln Met Asn
305                 310                 315                 320 agt ctg aga gcc gag gac acc gcc gtg tat tac tgt gca aaa gac tgg    1008
Ser Leu Arg Ala Glu Asp Thr Ala Val Tyr Tyr Cys Ala Lys Asp Trp
                325                 330                 335 gat aac tgg aac ctg ttt gac tac tgg ggc cag gga acc ctg gtc acc    1056
Asp Asn Trp Asn Leu Phe Asp Tyr Trp Gly Gln Gly Thr Leu Val Thr
            340                 345                 350 gtc tcc tca gcc tcc acc aag ggc cca tcg gtc ttc ccc ctg gca ccc    1104
Val Ser Ser Ala Ser Thr Lys Gly Pro Ser Val Phe Pro Leu Ala Pro
        355                 360                 365 tcc tcc aag agc acc tct ggg ggc aca gcg gcc ctg ggc tgc ctg gtc    1152
Ser Ser Lys Ser Thr Ser Gly Gly Thr Ala Ala Leu Gly Cys Leu Val
    370                 375                 380 aag gac tac ttc ccc gaa ccg gtg acg gtg tcg tgg aac tca ggc gcc    1200
Lys Asp Tyr Phe Pro Glu Pro Val Thr Val Ser Trp Asn Ser Gly Ala
385                 390                 395                 400 ctg acc agc ggc gtg cac acc ttc ccg gct gtc cta cag tcc tca gga    1248
Leu Thr Ser Gly Val His Thr Phe Pro Ala Val Leu Gln Ser Ser Gly
                405                 410                 415 ctc tac tcc ctt agt agc gtg gtg acc gtg ccc tcc agc agc ttg ggc    1296
Leu Tyr Ser Leu Ser Ser Val Val Thr Val Pro Ser Ser Ser Leu Gly
            420                 425                 430 acc cag acc tac atc tgc aac gtg aat cac aag ccc agc aac acc aag    1344
Thr Gln Thr Tyr Ile Cys Asn Val Asn His Lys Pro Ser Asn Thr Lys
        435                 440                 445 gtg gac aag aaa gtt gag ccc aaa tct tgt gac aaa act cac aca tgc    1392
Val Asp Lys Lys Val Glu Pro Lys Ser Cys Asp Lys Thr His Thr Cys
    450                 455                 460 cca ccg tgc cca gca cct gaa ctc ctg ggg gga ccg tca gtc ttc ctc    1440
Pro Pro Cys Pro Ala Pro Glu Leu Leu Gly Gly Pro Ser Val Phe Leu
465                 470                 475                 480 ttc ccc cca aaa ccc aag gac acc ctc atg atc tcc cgg acc cct gag    1488
Phe Pro Pro Lys Pro Lys Asp Thr Leu Met Ile Ser Arg Thr Pro Glu
                485                 490                 495 gtc aca tgc gtg gtg gtg gac gtg agc cac gaa gac cct gag gtc aag    1536
Val Thr Cys Val Val Val Asp Val Ser His Glu Asp Pro Glu Val Lys
            500                 505                 510 ttc aac tgg tac gtg gac ggc gtg gag gtg cat aat gcc aag aca aag    1584
Phe Asn Trp Tyr Val Asp Gly Val Glu Val His Asn Ala Lys Thr Lys
        515                 520                 525 ccg cgg gag gag cag tac aac agc acg tac cgt gtg gtc agc gtc ctc    1632
Pro Arg Glu Glu Gln Tyr Asn Ser Thr Tyr Arg Val Val Ser Val Leu
    530                 535                 540 acc gtc ctg cac cag gac tgg ctg aat ggc aag gag tac aag tgc aag    1680
Thr Val Leu His Gln Asp Trp Leu Asn Gly Lys Glu Tyr Lys Cys Lys
545                 550                 555                 560 gtc tcc aac aaa gcc ctc cca gcc ccc atc gag aaa acc atc tcc aaa    1728
Val Ser Asn Lys Ala Leu Pro Ala Pro Ile Glu Lys Thr Ile Ser Lys
                565                 570                 575 gcc aaa ggg cag ccc cga gaa cca cag gtg tac acc ctg ccc cca tcc    1776
Ala Lys Gly Gln Pro Arg Glu Pro Gln Val Tyr Thr Leu Pro Pro Ser
            580                 585                 590 cgg gat gag ctg acc aag aac cag gtc agc ctg acc tgc ctg gtc aaa    1824
Arg Asp Glu Leu Thr Lys Asn Gln Val Ser Leu Thr Cys Leu Val Lys
        595                 600                 605 ggc ttc tat ccc agc gac atc gcc gtg gag tgg gag agc aat ggg cag    1872
Gly Phe Tyr Pro Ser Asp Ile Ala Val Glu Trp Glu Ser Asn Gly Gln
```

```
Gly Phe Tyr Pro Ser Asp Ile Ala Val Glu Trp Glu Ser Asn Gly Gln
            610                 615                 620 ccg gag aac aac tac aag acc acg cct ccc gtg ctg gac tcc gac ggc      1920
Pro Glu Asn Asn Tyr Lys Thr Thr Pro Pro Val Leu Asp Ser Asp Gly
625                 630                 635                 640 tcc ttc ttc ctc tac agc aag ctc acc gtg gac aag agc agg tgg cag      1968
Ser Phe Phe Leu Tyr Ser Lys Leu Thr Val Asp Lys Ser Arg Trp Gln
                645                 650                 655 cag ggg aac gtc ttc tca tgc tcc gtg atg cat gag gct ctg cac aac      2016
Gln Gly Asn Val Phe Ser Cys Ser Val Met His Glu Ala Leu His Asn
            660                 665                 670 cac tac acg cag aag agc ctc tcc ctg tct ccg ggt aaa                  2055
His Tyr Thr Gln Lys Ser Leu Ser Leu Ser Pro Gly Lys
        675                 680                 685

<210> SEQ ID NO 2
<211> LENGTH: 685
<212> TYPE: PRT
<213> ORGANISM: Artificial Sequence
<220> FEATURE:
<223> OTHER INFORMATION: Synthetic Construct

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Phe
            20                  25                  30

Tyr Trp Thr Trp Ile Arg Gln Pro Pro Gly Lys Gly Leu Glu Trp Ile
        35                  40                  45

Gly Tyr Ile His Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Thr Leu Ser Ser Val Thr Ala Ala Asp Thr Ala Val Tyr Tyr Cys Ala
                85                  90                  95

Arg Arg Arg Ser Met Asn Trp Phe Asp Pro Trp Gly Gln Gly Thr Leu
            100                 105                 110

Val Ile Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Gly Gly Gly
    210                 215                 220

Gly Ser Gly Gly Gly Ser Gly Gly Gly Ser Glu Val Gln Leu
225                 230                 235                 240

Val Glu Ser Gly Gly Gly Leu Val Gln Pro Gly Gly Ser Leu Arg Leu
                245                 250                 255

Ser Cys Ala Ala Ser Gly Phe Thr Phe Asp Thr Tyr Ala Met His Trp
            260                 265                 270
```

```
Val Arg Gln Ala Pro Gly Lys Gly Leu Glu Trp Val Ala Gly Ile Ser
            275                 280                 285
Trp Asn Ser Gly Asn Ile Gly Tyr Ala Asp Ser Val Lys Gly Arg Phe
    290                 295                 300
Thr Ile Ser Arg Asp Asn Ser Lys Asn Thr Leu Tyr Leu Gln Met Asn
305                 310                 315                 320
Ser Leu Arg Ala Glu Asp Thr Ala Val Tyr Tyr Cys Ala Lys Asp Trp
                325                 330                 335
Asp Asn Trp Asn Leu Phe Asp Tyr Trp Gly Gln Gly Thr Leu Val Thr
            340                 345                 350
Val Ser Ser Ala Ser Thr Lys Gly Pro Ser Val Phe Pro Leu Ala Pro
        355                 360                 365
Ser Ser Lys Ser Thr Ser Gly Gly Thr Ala Ala Leu Gly Cys Leu Val
    370                 375                 380
Lys Asp Tyr Phe Pro Glu Pro Val Thr Val Ser Trp Asn Ser Gly Ala
385                 390                 395                 400
Leu Thr Ser Gly Val His Thr Phe Pro Ala Val Leu Gln Ser Ser Gly
                405                 410                 415
Leu Tyr Ser Leu Ser Ser Val Val Thr Val Pro Ser Ser Ser Leu Gly
            420                 425                 430
Thr Gln Thr Tyr Ile Cys Asn Val Asn His Lys Pro Ser Asn Thr Lys
        435                 440                 445
Val Asp Lys Lys Val Glu Pro Lys Ser Cys Asp Lys Thr His Thr Cys
    450                 455                 460
Pro Pro Cys Pro Ala Pro Glu Leu Leu Gly Gly Pro Ser Val Phe Leu
465                 470                 475                 480
Phe Pro Pro Lys Pro Lys Asp Thr Leu Met Ile Ser Arg Thr Pro Glu
                485                 490                 495
Val Thr Cys Val Val Val Asp Val Ser His Glu Asp Pro Glu Val Lys
            500                 505                 510
Phe Asn Trp Tyr Val Asp Gly Val Glu Val His Asn Ala Lys Thr Lys
        515                 520                 525
Pro Arg Glu Glu Gln Tyr Asn Ser Thr Tyr Arg Val Val Ser Val Leu
    530                 535                 540
Thr Val Leu His Gln Asp Trp Leu Asn Gly Lys Glu Tyr Lys Cys Lys
545                 550                 555                 560
Val Ser Asn Lys Ala Leu Pro Ala Pro Ile Glu Lys Thr Ile Ser Lys
                565                 570                 575
Ala Lys Gly Gln Pro Arg Glu Pro Gln Val Tyr Thr Leu Pro Pro Ser
            580                 585                 590
Arg Asp Glu Leu Thr Lys Asn Gln Val Ser Leu Thr Cys Leu Val Lys
        595                 600                 605
Gly Phe Tyr Pro Ser Asp Ile Ala Val Glu Trp Glu Ser Asn Gly Gln
    610                 615                 620
Pro Glu Asn Asn Tyr Lys Thr Thr Pro Pro Val Leu Asp Ser Asp Gly
625                 630                 635                 640
Ser Phe Phe Leu Tyr Ser Lys Leu Thr Val Asp Lys Ser Arg Trp Gln
                645                 650                 655
Gln Gly Asn Val Phe Ser Cys Ser Val Met His Glu Ala Leu His Asn
            660                 665                 670
His Tyr Thr Gln Lys Ser Leu Ser Leu Ser Pro Gly Lys
        675                 680                 685
```

<210> SEQ ID NO 3
<211> LENGTH: 1452
<212> TYPE: DNA
<213> ORGANISM: Artificial Sequence
<220> FEATURE:
<223> OTHER INFORMATION: L-chain fragment gene of tandem form a
<220> FEATURE:
<221> NAME/KEY: CDS
<222> LOCATION: (1)..(1452)

<400> SEQUENCE: 3

| | | | | | | | | | | | | | | | | |
|---|---|---|---|---|---|---|---|---|---|---|---|---|---|---|---|---|
| gcc | atc | cag | atg | acc | cag | tcc | ccc | tct | agc | ctg | tcc | gct | tcc | gtg | ggc | 48 |
| Ala | Ile | Gln | Met | Thr | Gln | Ser | Pro | Ser | Ser | Leu | Ser | Ala | Ser | Val | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gac | aga | gtg | acc | atc | acc | tgt | cgg | gcc | tct | caa | gtg | atc | cgg | aac | gac | 96 |
| Asp | Arg | Val | Thr | Ile | Thr | Cys | Arg | Ala | Ser | Gln | Val | Ile | Arg | Asn | Asp | |
| | | | 20 | | | | | 25 | | | | | 30 | | | |

| | | | | | | | | | | | | | | | | |
|---|---|---|---|---|---|---|---|---|---|---|---|---|---|---|---|---|
| ctg | ggc | tgg | tat | cag | cag | aag | cct | ggc | aag | gcc | ccc | aag | ttc | ctg | atc | 144 |
| Leu | Gly | Trp | Tyr | Gln | Gln | Lys | Pro | Gly | Lys | Ala | Pro | Lys | Phe | Leu | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| tac | gcc | gcc | tcc | agt | ctg | cag | tcc | ggc | gtg | ccc | tct | aga | ttc | tcc | ggc | 192 |
| Tyr | Ala | Ala | Ser | Ser | Leu | Gln | Ser | Gly | Val | Pro | Ser | Arg | Phe | Ser | Gly | |
| 50 | | | | | 55 | | | | | 60 | | | | | | |

| | | | | | | | | | | | | | | | | |
|---|---|---|---|---|---|---|---|---|---|---|---|---|---|---|---|---|
| tct | ggc | tct | ggc | acc | gac | ttt | acc | ctg | acc | atc | tcc | agc | ctg | cag | ccc | 240 |
| Ser | Gly | Ser | Gly | Thr | Asp | Phe | Thr | Leu | Thr | Ile | Ser | Ser | Leu | Gln | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gag | gac | ttc | gcc | acc | tac | tac | tgt | ctg | caa | gac | tac | aac | tac | ccc | ctg | 288 |
| Glu | Asp | Phe | Ala | Thr | Tyr | Tyr | Cys | Leu | Gln | Asp | Tyr | Asn | Tyr | Pro | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| acc | ttc | ggc | gga | ggc | acc | aag | gtg | gaa | atc | aag | cgg | acc | gtg | gcc | gct | 336 |
| Thr | Phe | Gly | Gly | Gly | Thr | Lys | Val | Glu | Ile | Lys | Arg | Thr | Val | Ala | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| ccc | tcc | gtg | ttc | atc | ttc | cca | cct | tcc | gac | gag | cag | ctg | aag | tcc | ggc | 384 |
| Pro | Ser | Val | Phe | Ile | Phe | Pro | Pro | Ser | Asp | Glu | Gln | Leu | Lys | Ser | Gly | |
| | | 115 | | | | | 120 | | | | | 125 | | | | |

| | | | | | | | | | | | | | | | | |
|---|---|---|---|---|---|---|---|---|---|---|---|---|---|---|---|---|
| acc | gct | tct | gtc | gtg | tgc | ctg | ctg | aac | aac | ttc | tac | ccc | cgc | gag | gcc | 432 |
| Thr | Ala | Ser | Val | Val | Cys | Leu | Leu | Asn | Asn | Phe | Tyr | Pro | Arg | Glu | Ala | |
| 130 | | | | | 135 | | | | | 140 | | | | | | |

| | | | | | | | | | | | | | | | | |
|---|---|---|---|---|---|---|---|---|---|---|---|---|---|---|---|---|
| aag | gtg | cag | tgg | aag | gtg | gac | aac | gcc | ctg | cag | agc | ggc | aac | tcc | cag | 480 |
| Lys | Val | Gln | Trp | Lys | Val | Asp | Asn | Ala | Leu | Gln | Ser | Gly | Asn | Ser | Gln | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gaa | tcc | gtg | acc | gag | cag | gac | tcc | aag | gac | agc | acc | tac | tcc | ctg | tcc | 528 |
| Glu | Ser | Val | Thr | Glu | Gln | Asp | Ser | Lys | Asp | Ser | Thr | Tyr | Ser | Leu | Ser | |
| | | | | 165 | | | | | 170 | | | | | 175 | | |

| | | | | | | | | | | | | | | | | |
|---|---|---|---|---|---|---|---|---|---|---|---|---|---|---|---|---|
| tcc | acc | ctg | acc | ctg | tcc | aag | gcc | gac | tac | gag | aag | cac | aag | gtg | tac | 576 |
| Ser | Thr | Leu | Thr | Leu | Ser | Lys | Ala | Asp | Tyr | Glu | Lys | His | Lys | Val | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| gcc | tgc | gaa | gtg | acc | cac | cag | ggc | ctg | tct | agc | ccc | gtg | acc | aag | tct | 624 |
| Ala | Cys | Glu | Val | Thr | His | Gln | Gly | Leu | Ser | Ser | Pro | Val | Thr | Lys | Ser | |
| | | 195 | | | | | 200 | | | | | 205 | | | | |

| | | | | | | | | | | | | | | | | |
|---|---|---|---|---|---|---|---|---|---|---|---|---|---|---|---|---|
| ttc | aac | cgg | ggc | gaa | tgt | ggc | ggc | gga | gga | tct | ggc | gga | ggt | gga | agc | 672 |
| Phe | Asn | Arg | Gly | Glu | Cys | Gly | Gly | Gly | Gly | Ser | Gly | Gly | Gly | Gly | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| gga | ggc | gga | ggt | agt | ggt | ggt | ggc | ggt | tct | ggc | gtg | cga | gct | aga | agg | 720 |
| Gly | Gly | Gly | Gly | Ser | Gly | Gly | Gly | Gly | Ser | Gly | Val | Arg | Ala | Arg | Arg | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gct | gct | cct | gtg | gga | ggg | ggc | gga | agt | ggg | gga | ggc | gga | tct | ggt | ggc | 768 |
| Ala | Ala | Pro | Val | Gly | Gly | Gly | Gly | Ser | Gly | Gly | Gly | Gly | Ser | Gly | Gly | |
| | | | | 245 | | | | | 250 | | | | | 255 | | |

| | | | | | | | | | | | | | | | | |
|---|---|---|---|---|---|---|---|---|---|---|---|---|---|---|---|---|
| gga | ggc | tca | ggt | ggc | ggt | gga | tct | cca | ggc | ggt | ggc | ggg | gga | gat | att | 816 |
| Gly | Gly | Ser | Gly | Gly | Gly | Gly | Ser | Pro | Gly | Gly | Gly | Gly | Gly | Asp | Ile | |

```
                            260                 265                 270
cag atg aca cag agc ccc agc tcc ctg agc gcc agc gtg gga gat cgc      864
Gln Met Thr Gln Ser Pro Ser Ser Leu Ser Ala Ser Val Gly Asp Arg
        275                 280                 285 gtg aca atc aca tgc cgg gcc agc cag tcc atc tcc tct tgg ctg gct      912
Val Thr Ile Thr Cys Arg Ala Ser Gln Ser Ile Ser Ser Trp Leu Ala
290                 295                 300 tgg tat cag cag aaa ccc gga aag gct cct aaa ctg ctg atc tac aag      960
Trp Tyr Gln Gln Lys Pro Gly Lys Ala Pro Lys Leu Leu Ile Tyr Lys
305                 310                 315                 320 gcc tcc tcc ctg gaa tct ggg gtg ccc tct cgg ttt tct ggc tcc ggc     1008
Ala Ser Ser Leu Glu Ser Gly Val Pro Ser Arg Phe Ser Gly Ser Gly
                325                 330                 335 agc ggc aca gac ttt aca ctg aca atc agc tcc ctg cag cct gaa gat     1056
Ser Gly Thr Asp Phe Thr Leu Thr Ile Ser Ser Leu Gln Pro Glu Asp
            340                 345                 350 ttt gct acc tat tac tgc cag cag tac tcc tcc tac tcc tgg acc ttt     1104
Phe Ala Thr Tyr Tyr Cys Gln Gln Tyr Ser Ser Tyr Ser Trp Thr Phe
        355                 360                 365 ggc cag gga aca aaa gtg gaa atc aaa cgc aca gtg gct gcc cca agc     1152
Gly Gln Gly Thr Lys Val Glu Ile Lys Arg Thr Val Ala Ala Pro Ser
370                 375                 380 gtg ttc att ttt ccc cca tct gat gaa cag ctg aaa agc ggc acc gca     1200
Val Phe Ile Phe Pro Pro Ser Asp Glu Gln Leu Lys Ser Gly Thr Ala
385                 390                 395                 400 agc gtc gtg tgt ctg ctg aac aat ttt tac cct agg gaa gct aaa gtg     1248
Ser Val Val Cys Leu Leu Asn Asn Phe Tyr Pro Arg Glu Ala Lys Val
                405                 410                 415 cag tgg aaa gtg gat aat gct ctg cag tct ggc aac agc cag gaa agt     1296
Gln Trp Lys Val Asp Asn Ala Leu Gln Ser Gly Asn Ser Gln Glu Ser
            420                 425                 430 gtg aca gaa cag gac agc aag gac tcc aca tac agc ctg tcc agc aca     1344
Val Thr Glu Gln Asp Ser Lys Asp Ser Thr Tyr Ser Leu Ser Ser Thr
        435                 440                 445 ctg aca ctg agc aag gct gat tat gag aaa cac aaa gtg tat gct tgt     1392
Leu Thr Leu Ser Lys Ala Asp Tyr Glu Lys His Lys Val Tyr Ala Cys
450                 455                 460 gaa gtg aca cat cag gga ctg agc agt cct gtg acc aag agc ttc aac     1440
Glu Val Thr His Gln Gly Leu Ser Ser Pro Val Thr Lys Ser Phe Asn
465                 470                 475                 480 aga ggc gag tgc                                                     1452
Arg Gly Glu Cys <210> SEQ ID NO 4
<211> LENGTH: 484
<212> TYPE: PRT
<213> ORGANISM: Artificial Sequence
<220> FEATURE:
<223> OTHER INFORMATION: Synthetic Construct

<400> SEQUENCE: 4

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Arg Asn Asp
            20                  25                  30

Leu Gly Trp Tyr Gln Gln Lys Pro Gly Lys Ala Pro Lys Phe Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Leu
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
210                 215                 220

Gly Gly Gly Gly Ser Gly Gly Gly Ser Gly Val Arg Ala Arg Arg
225                 230                 235                 240

Ala Ala Pro Val Gly Gly Gly Ser Gly Gly Gly Ser Gly Gly
                245                 250                 255

Gly Gly Ser Gly Gly Gly Gly Ser Pro Gly Gly Gly Gly Asp Ile
            260                 265                 270

Gln Met Thr Gln Ser Pro Ser Ser Leu Ser Ala Ser Val Gly Asp Arg
            275                 280                 285

Val Thr Ile Thr Cys Arg Ala Ser Gln Ser Ile Ser Ser Trp Leu Ala
        290                 295                 300

Trp Tyr Gln Gln Lys Pro Gly Lys Ala Pro Lys Leu Leu Ile Tyr Lys
305                 310                 315                 320

Ala Ser Ser Leu Glu Ser Gly Val Pro Ser Arg Phe Ser Gly Ser Gly
                325                 330                 335

Ser Gly Thr Asp Phe Thr Leu Thr Ile Ser Ser Leu Gln Pro Glu Asp
            340                 345                 350

Phe Ala Thr Tyr Tyr Cys Gln Gln Tyr Ser Ser Tyr Ser Trp Thr Phe
        355                 360                 365

Gly Gln Gly Thr Lys Val Glu Ile Lys Arg Thr Val Ala Ala Pro Ser
    370                 375                 380

Val Phe Ile Phe Pro Pro Ser Asp Glu Gln Leu Lys Ser Gly Thr Ala
385                 390                 395                 400

Ser Val Val Cys Leu Leu Asn Asn Phe Tyr Pro Arg Glu Ala Lys Val
                405                 410                 415

Gln Trp Lys Val Asp Asn Ala Leu Gln Ser Gly Asn Ser Gln Glu Ser
            420                 425                 430

Val Thr Glu Gln Asp Ser Lys Asp Ser Thr Tyr Ser Leu Ser Ser Thr
        435                 440                 445

Leu Thr Leu Ser Lys Ala Asp Tyr Glu Lys His Lys Val Tyr Ala Cys
    450                 455                 460

Glu Val Thr His Gln Gly Leu Ser Ser Pro Val Thr Lys Ser Phe Asn
465                 470                 475                 480

Arg Gly Glu Cys
```

```
<210> SEQ ID NO 5
<211> LENGTH: 10
<212> TYPE: PRT
<213> ORGANISM: Artificial Sequence
<220> FEATURE:
<223> OTHER INFORMATION: Protease recognition sequence

<400> SEQUENCE: 5

Gly Val Arg Ala Arg Arg Ala Ala Pro Val
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Protease recognition sequence

<400> SEQUENCE: 6

Gly Leu Arg Leu Pro Arg Glu Thr Asp Glu
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Protease recognition sequence

<400> SEQUENCE: 7

Arg Lys Arg Lys Arg Arg
1               5

<210> SEQ ID NO 8
<211> LENGTH: 6
<212> TYPE: PRT
<213> ORGANISM: Artificial Sequence
<220> FEATURE:
<223> OTHER INFORMATION: Protease recognition sequence

<400> SEQUENCE: 8

Arg Ser Arg Lys Arg Arg
1               5

<210> SEQ ID NO 9
<211> LENGTH: 56
<212> TYPE: PRT
<213> ORGANISM: Artificial Sequence
<220> FEATURE:
<223> OTHER INFORMATION: Linker of L-chain fragment

<400> SEQUENCE: 9

Gly Gly Gly Gly Ser Gly Gly Gly Ser Gly Gly Gly Ser Gly
1               5                   10                  15

Gly Gly Gly Ser Gly Val Arg Ala Arg Arg Ala Ala Pro Val Gly Gly
                20                  25                  30

Gly Gly Ser Gly Gly Gly Gly Ser Gly Gly Gly Gly Ser Gly Gly Gly
            35                  40                  45

Gly Ser Pro Gly Gly Gly Gly Gly
        50                  55

<210> SEQ ID NO 10
<211> LENGTH: 56
<212> TYPE: PRT
```

<213> ORGANISM: Artificial Sequence
<220> FEATURE:
<223> OTHER INFORMATION: Linker of L-chain fragment

<400> SEQUENCE: 10

Gly Gly Gly Gly Ser Gly Gly Gly Ser Gly Gly Gly Gly Ser Gly
1               5                   10                  15

Gly Gly Gly Ser Gly Leu Arg Leu Pro Arg Glu Thr Asp Glu Gly
                20                  25                  30

Gly Gly Ser Gly Gly Gly Gly Ser Gly Gly Gly Ser Gly Gly Gly
            35                  40                  45

Gly Ser Pro Gly Gly Gly Gly Gly
        50                  55

<210> SEQ ID NO 11
<211> LENGTH: 52
<212> TYPE: PRT
<213> ORGANISM: Artificial Sequence
<220> FEATURE:
<223> OTHER INFORMATION: Linker of L-chain fragment

<400> SEQUENCE: 11

Gly Gly Gly Gly Ser Gly Gly Gly Ser Gly Gly Gly Gly Ser Gly
1               5                   10                  15

Gly Gly Gly Ser Arg Lys Arg Lys Arg Gly Gly Gly Gly Ser Gly
                20                  25                  30

Gly Gly Gly Ser Gly Gly Gly Gly Ser Gly Gly Gly Ser Pro Gly
            35                  40                  45

Gly Gly Gly Gly
        50

<210> SEQ ID NO 12
<211> LENGTH: 52
<212> TYPE: PRT
<213> ORGANISM: Artificial Sequence
<220> FEATURE:
<223> OTHER INFORMATION: Linker of L-chain fragment

<400> SEQUENCE: 12

Gly Gly Gly Gly Ser Gly Gly Gly Gly Ser Gly Gly Gly Ser Gly
1               5                   10                  15

Gly Gly Gly Ser Arg Ser Arg Lys Arg Gly Gly Gly Gly Ser Gly
                20                  25                  30

Gly Gly Gly Ser Gly Gly Gly Gly Ser Gly Gly Gly Ser Pro Gly
            35                  40                  45

Gly Gly Gly Gly
        50

<210> SEQ ID NO 13
<211> LENGTH: 8
<212> TYPE: PRT
<213> ORGANISM: Artificial Sequence
<220> FEATURE:
<223> OTHER INFORMATION: PreScission Protease sequence

<400> SEQUENCE: 13

Leu Glu Val Leu Phe Gln Gly Pro
1               5